United States Patent
Dolan et al.

(10) Patent No.: US 11,981,635 B2
(45) Date of Patent: May 14, 2024

(54) HYDROCARBON RECOVERY UNITS WITH SEPARATORS CONFIGURED TO REDUCE LIQUID HYDROCARBON EXPOSURE TO REGENERATION GAS STREAMS

(71) Applicant: BASF CORPORATION, Florham Park, NJ (US)

(72) Inventors: William B. Dolan, Iselin, NJ (US); Tobias Eckardt, Nienburg/Weser (DE); Justin Pan, Iselin, NJ (US); Manish Mehta, Abu Dhabi (AE)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 18/266,488

(22) PCT Filed: Dec. 12, 2021

(86) PCT No.: PCT/US2021/062993
§ 371 (c)(1),
(2) Date: Jun. 9, 2023

(87) PCT Pub. No.: WO2022/140088
PCT Pub. Date: Jun. 30, 2022

(65) Prior Publication Data
US 2023/0391692 A1    Dec. 7, 2023

Related U.S. Application Data

(60) Provisional application No. 63/189,294, filed on May 17, 2021, provisional application No. 63/128,688, filed on Dec. 21, 2020.

(51) Int. Cl.
*C07C 7/12* (2006.01)
*B01D 53/00* (2006.01)
(Continued)

(52) U.S. Cl.
CPC ............. *C07C 7/12* (2013.01); *B01D 53/002* (2013.01); *B01D 53/0462* (2013.01);
(Continued)

(58) Field of Classification Search
None
See application file for complete search history.

(56) References Cited

U.S. PATENT DOCUMENTS 3,479,797 A * 11/1969 Greathouse ............ B01D 53/04
95/146
2006/0204419 A1  9/2006 Thomas et al.
(Continued)

FOREIGN PATENT DOCUMENTS

WO    2021/263216 A1    12/2021

OTHER PUBLICATIONS

International Search Report and Written Opinion of International Application No. PCT/US2021/062993 dated Mar. 2, 2022, 9 pgs.

*Primary Examiner* — Tam M Nguyen
(74) *Attorney, Agent, or Firm* — LOWENSTEIN SANDLER LLP

(57) ABSTRACT

Disclosed in certain embodiments are processes for heavy hydrocarbon removal that implement a regeneration loop to reduce an amount of liquid hydrocarbons exposed by the separator to the regeneration stream over one or more durations for which an average C5+ hydrocarbon content of the regeneration stream is reduced or minimal.

8 Claims, 16 Drawing Sheets

(51) Int. Cl.
 *B01D 53/04* (2006.01)
 *B01D 53/26* (2006.01)
(52) U.S. Cl.
 CPC ........ *B01D 53/265* (2013.01); *B01D 2256/24* (2013.01); *B01D 2257/306* (2013.01); *B01D 2257/702* (2013.01); *B01D 2257/80* (2013.01); *B01D 2259/40052* (2013.01)

(56) References Cited

U.S. PATENT DOCUMENTS

| | | |
|---|---|---|
| 2007/0267328 A1 | 11/2007 | Neumann et al. |
| 2013/0192299 A1* | 8/2013 | Dolan ................ C10G 5/02 62/636 |
| 2014/0033763 A1 | 2/2014 | Chen et al. |
| 2017/0056811 A1* | 3/2017 | Nagavarapu ....... B01D 53/0407 |
| 2017/0056813 A1* | 3/2017 | McMahon ........... B01D 53/047 |
| 2019/0275460 A1* | 9/2019 | Zhong ................ B01D 53/0476 |
| 2020/0370824 A1* | 11/2020 | Mak ....................... F25J 3/0238 |
| 2021/0213384 A1* | 7/2021 | Ghanbari ................ C10L 3/106 |
| 2021/0339187 A1 | 11/2021 | Dolan et al. |
| 2022/0298443 A1* | 9/2022 | Tazi ..................... B01D 53/047 |
| 2023/0201758 A1* | 6/2023 | Grahl ...................... C10G 5/02 95/139 |
| 2023/0249119 A1* | 8/2023 | Casteel, Jr. ............. C01B 3/508 62/617 |

* cited by examiner

HYDROCARBON RECOVERY UNITS WITH SEPARATORS CONFIGURED TO REDUCE LIQUID HYDROCARBON EXPOSURE TO REGENERATION GAS STREAMS

CROSS-REFERENCE TO RELATED APPLICATION(S)

This application claims the benefit of priority of U.S. Provisional Patent Application No. 63/189,294, filed on May 17, 2021, and U.S. Provisional Patent Application No. 63/128,688, filed on Dec. 21, 2020, the disclosures of which are hereby incorporated by reference herein in their entireties.

BACKGROUND

Hydrocarbon recovery units (HRUs) generally utilize one or more adsorbent beds during hydrocarbon adsorption, while at the same time one or more adsorbent beds are regenerated via a regeneration loop. The regeneration loop utilizes a heating step followed by a cooling step with the feed gas stream or a treated gas stream being used as the regeneration gas. Contaminants are subsequently removed as liquids from the regeneration gas during cooling via a condenser while the separated regeneration gas is recycled to the feed side of the one or more beds in adsorption and mixed with the feed gas. The regeneration process can be adjusted for specific adsorbent mass and cycle time such that one or more contaminants is preferentially removed. If certain contaminants are not adequately removed by the separation, excess contaminants can be reintroduced into the feed gas, thus resulting in a higher concentration of contaminants at the feed side of the one or more adsorbent beds. Moreover, if the regenerated gas is exposed to a liquid hydrocarbon phase in a separation unit ("separator") at a point at which heavy hydrocarbons (e.g., C5+) are not present in the gas phase, this can result in contamination of the regenerated gas by vaporized heavy hydrocarbons from the liquid hydrocarbon phase.

BRIEF DESCRIPTION OF THE DRAWINGS

The present disclosure is illustrated by way of example, and not by way of limitation, in the figures of the accompanying drawings, in which.

SUMMARY

Figure 1:
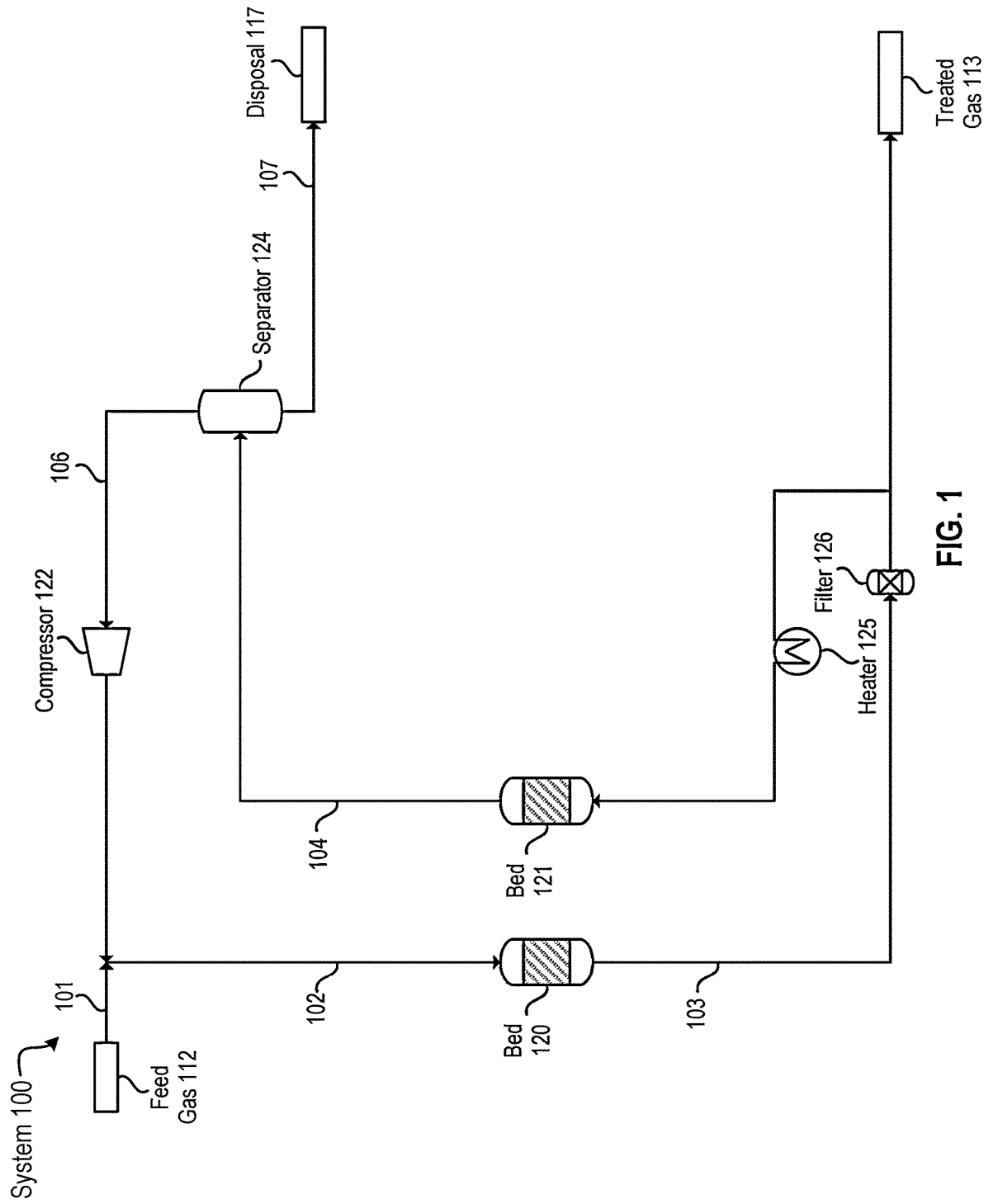
FIG. 1 illustrates a schematic of a system 100 for hydrocarbon removal using a single separator.

The following summary presents a simplified summary of various aspects of the present disclosure in order to provide a basic understanding of such aspects. This summary is not an extensive overview of the disclosure. It is intended to neither identify key or critical elements of the disclosure, nor delineate any scope of the particular embodiments of the disclosure or any scope of the claims. Its sole purpose is to present some concepts of the disclosure in a simplified form as a prelude to the more detailed description that is presented later.

In one aspect of the present disclosure, a process comprises: introducing a feed gas stream comprising C5+ hydrocarbons or organic sulfur species into a first adsorbent bed to produce a treated gas stream; regenerating a second adsorbent bed with a portion of the treated gas stream to produce a regeneration gas stream; introducing the regeneration stream into a separator to separate a gaseous phase of the regeneration gas stream from liquid hydrocarbon and/or liquid water phases; reducing an amount of liquid hydrocarbons exposed by the separator to the regeneration stream over one or more durations for which an average C5+ hydrocarbon content of the regeneration stream is reduced or minimal; and mixing the separated gaseous phase with the feed gas stream.

In another aspect of the present disclosure, a process comprises introducing a feed gas stream comprising C5+ hydrocarbons or organic sulfur species into a first adsorbent bed to produce a treated gas stream; regenerating a second adsorbent bed with a portion of the treated gas stream to produce a regeneration gas stream; introducing the regeneration stream into a separator to separate a gaseous phase of the regeneration gas stream from liquid hydrocarbon and/or liquid water phases; reducing an amount of liquid hydrocarbons exposed by the separator to the regeneration stream; and mixing the separated gaseous phase with the feed gas stream. In at least one embodiment, a fractional improvement ($FracImp_{hc}$) of hydrocarbon production for the process is at least 20%, at least 40%, at least 60%, at least 80%, or at least 100%, and the fractional improvement of hydrocarbon production is defined according to:

$$FracImp_{hc} = \left( \frac{Actual_{hc} - Base_{hc}}{Max_{hc} - Base_{hc}} \right),$$

where: $Actual_{hc}$ is an actual hydrocarbon production yield of the process, $Base_{hc}$ is a base case hydrocarbon yield when an average composition of the regeneration gas stream over the heating step is allowed to condense in the separator without reducing the amount of liquid hydrocarbons exposed by the separator to the regeneration stream, and $\text{Max}_{hc}$ is a best-case hydrocarbon yield for which liquids are instantaneously removed from the separator.

In at least one embodiment, a first duration of the one or more durations ends before a peak mole fraction of a C5 or C6 hydrocarbon peak in the gaseous phase is reached. In at least one embodiment, the first duration ends before 50%, before 40%, before 30%, before 20%, or before 10% of the peak mole fraction of the C5 or C6 hydrocarbon peak in the gaseous phase is reached.

In at least one embodiment, a second duration of the one or more durations begins after a peak mole fraction of a C7, C8, or C9 hydrocarbon peak in the gaseous phase is reached. In at least one embodiment, the second duration begins after 50%, after 40%, after 30%, after 20%, or after 10% of the peak mole fraction of the C7, C8, or C9 hydrocarbon peak in the gaseous phase is reached.

In at least one embodiment, reducing the amount of liquid hydrocarbons exposed by the separator to the gaseous phase comprises reducing the surface area of liquid hydrocarbons in the separator during the one or more durations. In at least one embodiment, reducing the surface area comprises lowering a liquid level control setpoint.

In at least one embodiment, reducing the amount of liquid hydrocarbons exposed by the separator to the gaseous phase comprises bypassing the separator before or during the one or more durations.

In at least one embodiment, reducing the amount of liquid hydrocarbons exposed by the separator to the gaseous phase comprises reducing a volume of exposed liquid hydrocarbons in the separator before or during the one or more durations.

In at least one embodiment, at least a portion of the treated gas stream is used for liquid natural gas production.

In at least one embodiment, at least a portion of the treated gas stream is part of or provided to a natural gas pipeline.

In at least one embodiment, at least a portion of the treated gas stream is diverted to underground storage.

In at least one embodiment, at least a portion of the treated gas stream is diverted to a membrane purification unit for $CO_2$ removal.

In at least one embodiment, one or more of the first or second adsorbent bed comprises an amorphous silica adsorbent and/or an amorphous silica-alumina adsorbent.

In at least one embodiment, the second adsorbent bed comprises a high-silica zeolite adsorbent. In at least one embodiment, the high-silica zeolite adsorbent comprises ZSM-5, zeolite Y, or beta zeolite.

In at least one embodiment, the second adsorbent bed comprises one or more of zeolite 3A, zeolite 4A, zeolite 5A, or zeolite X. In at least one embodiment, the second adsorbent bed comprises zeolite 13X. In at least one embodiment, one or more of the zeolites is exchanged with an element selected from Li, Na, K, Mg, Ca, Sr, or Ba.

In another aspect of the present disclosure, a system comprises: an adsorbent bed configured to receive a treated stream to regenerate the adsorbent bed; a separator configured to receive a regeneration stream from the adsorbent bed, the separator being configured to separate the regeneration stream into a gas stream, a condensed hydrocarbon stream, and a water stream; and a plurality of valves configured to cause the regeneration stream to bypass the separator and reduce an amount of liquid hydrocarbons exposed by the separator to the regeneration stream over one or more durations for which an average C5+ hydrocarbon content of the regeneration stream is reduced or minimal.

In another aspect of the present disclosure, a system comprises: an adsorbent bed configured to receive a treated stream to regenerate the adsorbent bed; a first separator configured to receive a regeneration stream from the adsorbent bed; and a second separator configured to receive the regeneration stream from the adsorbent bed, each of the first separator and the second separator being configured to separate the regeneration stream into a gas stream and a condensed hydrocarbon stream; and a plurality of valves configured to bypass the first separator and divert the regeneration stream to the second separator over a duration for which an average C5+ hydrocarbon content of the regeneration stream is reduced or minimal.

In another aspect of the present disclosure, a system comprises: an adsorbent bed configured to receive a treated stream to regenerate the adsorbent bed; a first separator configured to receive a regeneration stream from the adsorbent bed, the first separator being configured to separate the regeneration stream into a gas stream and a condensed hydrocarbon stream; and a second separator configured to receive the condensed hydrocarbon stream from the first separator and maintain a minimal amount of condensed hydrocarbons in the first separator.

In another aspect of the present disclosure, a system comprises: an adsorbent bed configured to receive a treated stream to regenerate the adsorbent bed; a first separator first separator configured to receive a regeneration stream from the adsorbent bed, the first separator being configured to separate the regeneration stream into a gas stream and a condensed hydrocarbon stream, and the first separator being configured to maintain a residence time of condensed hydrocarbons from 0.5 minutes to 60 minutes; and a second separator configured to receive the condensed hydrocarbon stream from the first separator.

In another aspect of the present disclosure, a system comprises: an adsorbent bed configured to receive a treated stream to regenerate the adsorbent bed; a first separator configured to receive a regeneration stream from the adsorbent bed, the first separator being configured to separate the regeneration stream into a gas stream and a condensed hydrocarbon stream; a second separator configured to receive the condensed hydrocarbon stream from the first separator; and a plurality of valves configured to bypass the first separator and the second separator and divert the regeneration stream over a duration for which an average C5+ hydrocarbon content of the regeneration stream is reduced or minimal.

In another aspect of the present disclosure, a system comprises: an adsorbent bed configured to receive a treated stream to regenerate the adsorbent bed; and a separator comprising: an inlet to receive a regeneration stream from the adsorbent bed into a vapor phase compartment; a downcomer adapted to separate liquid hydrocarbons from the vapor phase and divert the liquid hydrocarbons to a liquid phase compartment; a first outlet from the vapor phase compartment to return the vapor phase to the adsorbent bed; a chimney for diverting vapor from the liquid phase compartment to a second outlet; a third outlet to drain liquid hydrocarbons from the liquid phase compartment; a fourth outlet to drain liquid water from the liquid phase compartment; and a level sensor configured to maintain and adjust a level of the liquid hydrocarbons in the liquid phase compartment.

In another aspect of the present disclosure, a system comprises: an adsorbent bed configured to receive a treated stream to regenerate the adsorbent bed; and a separator configured to receive a regeneration stream from the adsorbent bed, the separator being configured to separate the regeneration stream into a gas stream and a condensed hydrocarbon stream, the separator being configured to maintain a minimum residence time of condensed hydrocarbons from 0.5 minutes to 60 minutes for all liquid hydrocarbon inlet flows, and the separator being configured to reduce a level setpoint of liquid hydrocarbons in response to a peak inlet hydrocarbon flow being observed or detected.

In another aspect of the present disclosure, a system comprises: an adsorbent bed configured to receive a treated stream to regenerate the adsorbent bed; and a separator configured to receive a regeneration stream from the adsorbent bed, the separator is being to separate the regeneration stream into a gas stream and a condensed hydrocarbon stream, the separator being configured to maintain a level setpoint of liquid hydrocarbons that meets a minimum residence time of 0.5 minutes to 60 minutes for all liquid hydrocarbon inlet flows, and the separator being configured to reduce the hydrocarbon level setpoint by 5% to 95% in response to a peak inlet hydrocarbon flow being observed or detected.

In at least one embodiment, the system is configured to reduce the hydrocarbon level setpoint by 5% to 10%, by 10% to 15%, 15% to 20%, by 20% to 25%, 25% to 30%, by 30% to 35%, 35% to 40%, by 40% to 45%, 45% to 50%, by 50% to 55%, 55% to 60%, by 60% to 65%, 65% to 70%, by 70% to 75%, 75% to 80%, by 80% to 85%, by 85% to 90%, by 90% to 95%, or within any subrange defined therebetween.

In another aspect of the present disclosure, a system comprises: an adsorbent bed configured to receive a treated stream to regenerate the adsorbent bed; a separator configured to receive a regeneration stream from the adsorbent bed, the separator being configured to separate the regeneration stream into a gas stream and a condensed hydrocarbon stream, the separator being configured to maintain a volume of liquid hydrocarbons that meets a minimum residence time of 0.5 minutes to 60 minutes for all liquid hydrocarbon inlet flows, and the separator being configured to reduce a volume of stored liquid hydrocarbons by 5% to 95% in response to a peak inlet hydrocarbon flow being observed or detected.

In at least one embodiment, the system is configured to reduce the volume of stored liquid hydrocarbons by 5% to 10%, by 10% to 15%, 15% to 20%, by 20% to 25%, 25% to 30%, by 30% to 35%, 35% to 40%, by 40% to 45%, 45% to 50%, by 50% to 55%, 55% to 60%, by 60% to 65%, 65% to 70%, by 70% to 75%, 75% to 80%, by 80% to 85%, by 85% to 90%, by 90% to 95%, or within any subrange defined therebetween.

In at least one embodiment, the minimum residence time of any of the aforementioned systems is from 0.5 minutes to 1 minute, 1 minute to 1.5 minutes, 1.5 minutes to 2 minutes, 2 minutes to 2.5 minutes, 2.5 minutes to 3 minutes, 3 minutes to 3.5 minutes, 3.5 minutes to 4 minutes, 4 minutes to 4.5 minutes, 4.5 minutes to 5 minutes, 5 minutes to 5.5 minutes, 5.5 minutes to 6 minutes, 6 minutes to 6.5 minutes, 6.5 minutes to 7 minutes, 7 minutes to 7.5 minutes, 7.5 minutes to 8 minutes, 8 minutes to 8.5 minutes, 8.5 minutes to 9 minutes, 9 minutes to 9.5 minutes, 9.5 minutes to 10 minutes, or within any subrange defined therebetween.

DETAILED DESCRIPTION

The present disclosure relates generally to systems and processes for heavy hydrocarbon removal. Specifically, certain embodiments include a regeneration loop that reduces or minimizes an amount of liquid hydrocarbons (e.g., C5+ or C6+ hydrocarbons and/or mercaptans) exposed by a separator to a gas phase over durations at which hydrocarbons in the separator are no longer being condensed into liquid hydrocarbons (e.g., when a mole fraction of heavy hydrocarbon gaseous species entering the separator is reduced or minimal). For example, in certain embodiments the separator can be bypassed at this point. The embodiments described herein advantageously reduce the amount of build-up of heavy hydrocarbons and mercaptans from a gas stream of the regeneration loop when re-introduced into an adsorbent bed together with a feed gas stream during an adsorption cycle.

The adsorption process of the present disclosure, used to remove mercaptans, heavy hydrocarbons (e.g., C5+ or C6+ components), and/or water from gas feed streams (e.g., a natural gas feed streams), may be accomplished by thermal swing adsorption (TSA). TSA processes are generally known in the art for various types of adsorptive separations. Generally, TSA processes utilize the process steps of adsorption at a low temperature, regeneration at an elevated temperature with a hot purge gas, and a subsequent cooling down to the adsorption temperature. TSA processes are often used for drying gases and liquids and for purification where trace impurities are to be removed. TSA processes are often employed when the components to be adsorbed are strongly adsorbed on the adsorbent, and thus heat is required for regeneration. A typical TSA process includes adsorption cycles and regeneration (desorption) cycles, each of which may include multiple adsorption steps and regeneration steps, as well as cooling steps and heating steps. The regeneration temperature is higher than the adsorption temperature in order to effect desorption of water, mercaptans, and heavy hydrocarbons.

In the regeneration step, part of one of the gas streams (e.g., a stream of natural gas), the product effluent from the adsorption unit, or a waste stream from a downstream process can be heated, and the heated stream is circulated through the adsorbent to desorb the adsorbed components. In some embodiments, it is advantageous to employ a hot purge stream comprising a heated raw natural gas stream for regeneration of the adsorbent.

In some embodiments, the pressures used during the adsorption and regeneration steps are generally elevated at typically 700 to 1500 psig. Typically, heavy hydrocarbon adsorption is carried out at pressures close to that of the feed stream and the regeneration steps may be conducted at about the adsorption pressure or at a reduced pressure. When a portion of an adsorption effluent stream is used as a purge gas, the regeneration may be advantageously conducted at about the adsorption pressure, especially when the waste or purge stream is re-introduced into the raw natural gas stream, for example.

As used herein, a "mercaptan" refers to an organic sulfur-containing compound including, but not limited to, methyl mercaptans (C1-RSH), ethyl mercaptans (C2-RSH), propyl mercaptans (C3-RSH), butyl mercaptans (C4-RSH), dimethyl sulfide (DMS), and dimethyl disulfide (DMDS).

While some embodiments of the present disclosure are described with respect to natural gas purification processes, it is to be understood by those of ordinary skill in the art that the embodiments herein may be utilized in or adapted for use in other types of industrial applications that require hydrocarbon removal.

FIG. 1 illustrates a schematic of a system 100 for hydrocarbon removal using a single separator 124. The system 100 includes a feed gas 112 source to direct a feed gas along a stream 101. A stream 102 is directed to an adsorbent bed 120, for example, during an adsorption cycle of a TSA process. A gas composition of stream 102 corresponds to the gas composition of stream 101. In some embodiments, the gas composition of stream 102 corresponds to a mixture of stream 101 and stream 106, which is a regeneration gas stream. A stream 103 leaving the adsorbent bed passes through a filter 126 (e.g., a dust filter) and is split into two paths: a first path to collect treated gas 113 and a second path that uses a portion of treated gas 113 as part of a regeneration loop. The second path may pass through a heater 125 to heat the treated gas to facilitate desorption in an adsorbent bed 121. A regeneration gas stream 104 leaving the adsorbent bed 121 is then directed along a stream 104 to the separator 124 to separate and remove heavy hydrocarbons 107 and/or water (e.g., via disposal 117). A separated regeneration gas stream 106 passes through a compressor 122 before being mixed with stream 101 and reintroduced into the adsorbent bed 120.

Figure 2:
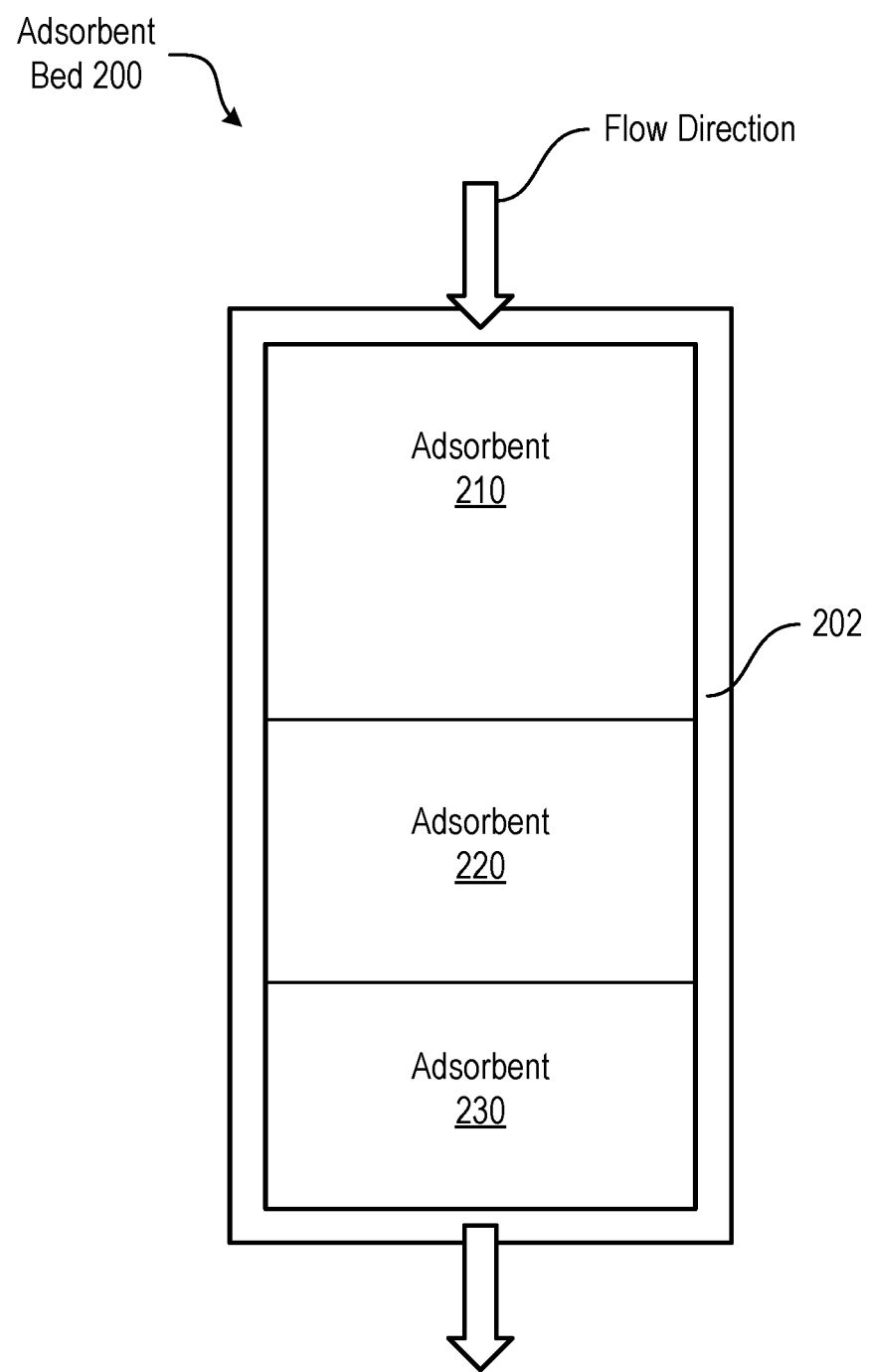
FIG. 2 illustrates an adsorbent bed for use in accordance with at least one embodiment of the disclosure.

FIG. 2 illustrates an adsorbent bed 200 in accordance with a first embodiment of the disclosure, which may be adapted for use in a TSA process. The adsorbent bed 200 may be representative of one or more of the adsorbent beds 120 or 121. The adsorbent bed 200 includes an adsorbent layer 210, an adsorbent layer 220, and an adsorbent layer 230 each contained inside a vessel 202. The three adsorbents are merely illustrative, and it is to be understood that any suitable number of distinct adsorbent layers may be utilized (e.g., a single layer, two layers, etc.). The flow direction indicates the flow of a gas feed stream through an inlet of the vessel 202, through the adsorbent layer 210, through the adsorbent layer 220, and then through adsorbent layer 230 before reaching an outlet of the vessel 202. The adsorbent layer 220 is said to be downstream from the adsorbent layer 210 based on this flow direction. Similarly, the adsorbent 230 is said to be downstream from the adsorbent layer 220. In some embodiments, each adsorbent layer may comprise their respective adsorbents in a form of adsorbent beads having diameters, for example, from about 1 mm to about 5 mm. The relative sizes of the adsorbent layers is not necessarily drawn to scale, though in certain embodiments a weight percent (wt. %) of the adsorbent layer 210 with respect to a total weight of the adsorbent bed 200 (i.e., a total weight of the adsorbent layer 210, the adsorbent layer 220, and the adsorbent layer 230) may be greater than 50 wt. %, greater than 60 wt. %, greater than 70 wt. %, greater than 80 wt. %, or greater than 90 wt. %.

In some embodiments, one or more of the adsorbent layers 210, 220, or 230 comprise an adsorbent that is preferentially selective for C5+ or C6+ hydrocarbons. In some embodiments, one or more of the adsorbent layers 210, 220, or 230 comprise an adsorbent that is preferentially selective for mercaptans. As used herein, the terms "preferentially selective for" or "selective for" indicates that the adsorbent adsorbs the specified compound at a greater equilibrium loading compared to methane, further described by the following equation: selectivity=(loading C6+/concentration C6+)/(loading C1/concentration C1), where C1 is methane, and where loading is defined as moles of component adsorbed/gram of adsorbent. In certain embodiments, C5+ or C6+ compounds may comprise one or more of pentane, hexane, benzene, heptane, octane, nonane, toluene, ethylbenzene, xylene, or neopentane.

In some embodiments, one or more of the adsorbent layers 210, 220, or 230 comprise one or more of an amorphous silica adsorbent, an amorphous silica-alumina adsorbent, or a high-silica zeolite adsorbent. In some embodiments, one or more of the adsorbent layers 210, 220, or 230 comprise an amorphous silica adsorbent and/or an amorphous silica-alumina adsorbent. Amorphous silica adsorbents and amorphous silica-alumina adsorbents may be at least partially crystalline. In some embodiments, an amorphous silica adsorbents or an amorphous silica-alumina adsorbent may be at least 50% amorphous, at least 60% amorphous, at least 70% amorphous, at least 80% amorphous, at least 90% amorphous, or 100% amorphous. In some embodiments, an amorphous silica adsorbents or an amorphous silica-alumina adsorbent may further include other components, such as adsorbed cations. In some embodiments, one or more of the adsorbent layers 210, 220, or 230 comprise a high-silica zeolite adsorbent, such as beta zeolite, ZSM-5, Y zeolite, or combinations thereof. As used herein, "high-silica zeolite" refers to a material having a silica-to-alumina ratio, on a molar basis, of at least 5, of at least 10, of at least 20, at least 30, at least 50, at least 100, at least 150, at least 200, at least 250, at least 300, at least 350, at least 400, at least 450, or at least 500. In some embodiments, the silica to alumina ratio is in the range of from 20 to 500.

In some embodiments, one or more of the adsorbent layers 210, 220, or 230 comprise one or more of zeolite A, zeolite X (e.g., zeolite 13X, which is zeolite X that has been exchanged with sodium ions), or zeolite Y. In some embodiments, one or more of the adsorbent layers 210, 220, or 230 comprise one or more of zeolite 3A, zeolite 4A, zeolite 5A, or zeolite X. In some embodiments, the zeolite is exchanged with any element of columns I and II of the periodic table, such as Li, Na, K, Mg, Ca, Sr, or Ba. In some embodiments, one or more of the adsorbent layers 210, 220, or 230 comprise one or more of zeolite 5A or zeolite X. In some embodiments, the zeolite is exchanged with any element of columns I and II of the periodic table, such as Li, Na, K, Mg, Ca, Sr, or Ba. In some embodiments, the adsorbent layer 230 comprises zeolite X, and the zeolite X is zeolite 13X (i.e., zeolite X that has been exchanged with sodium ions).

Exemplary adsorbents for one or more of the adsorbent layers 210, 220, or 230 may include one or more of Durasorb™ HD, Durasorb™ BTX, Durasorb™ HC, Durasorb™ AR, or Durasorb™ HR4 (available from BASF).

Figure 3:
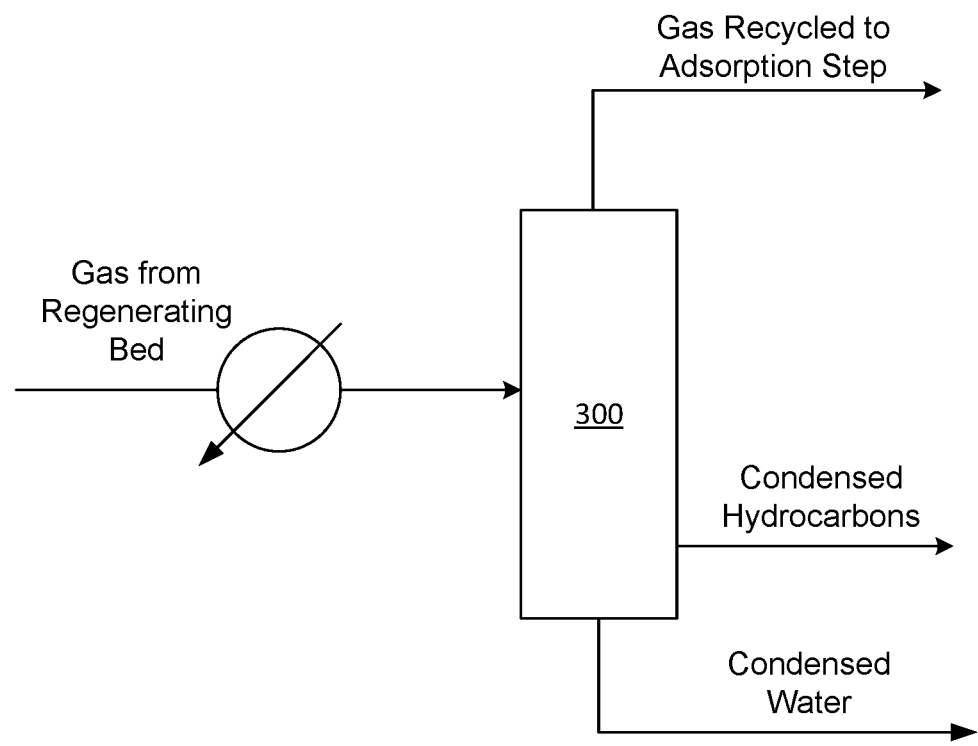
FIG. 3 is a schematic of a standard separator for use in various embodiments.

FIG. 3 is a schematic of a standard separator 300, which may be representative of the separator 124. The separator 300 is depicted as a three-phase separator that separates gas from a regenerating adsorbent bed into gas recycled to an adsorbing adsorbent bed (a separated regeneration gas stream), condensed (liquid) hydrocarbons, and liquid water. Current approaches allow the separator to operate during the regeneration process (e.g., regeneration of the adsorbent bed 121). If the separator is large, then during a portion of the regeneration cycle when no hydrocarbons are being condensed out of the gas stream leaving the adsorbent bed being regenerated (e.g., the bed 121), the separator can introduce hydrocarbons (e.g., C5+ hydrocarbons) back into the regeneration gas stream (e.g., the stream 106) that is sent to the adsorbing adsorbent bed (e.g., the adsorbent bed 120).

Certain embodiments of the present disclosure relate to regeneration processes that reduce an amount of liquid hydrocarbons exposed by the separator to a regeneration stream. In one embodiment, a process comprises: introducing a feed gas stream comprising C5+ hydrocarbons or organic sulfur species into a first adsorbent bed to produce a treated gas stream; regenerating a second adsorbent bed with a portion of the treated gas stream to produce a regeneration gas stream; introducing the regeneration stream into a separator to separate a gaseous phase of the regeneration gas stream from liquid hydrocarbon and/or liquid water phases; reducing an amount of liquid hydrocarbons exposed by the separator to the regeneration stream over one or more durations for which an average C5+ hydrocarbon content of the regeneration stream is reduced or minimal; and mixing the separated gaseous phase with the feed gas stream. In some embodiments, the amount of liquid hydrocarbons exposed by the separator to the regeneration stream can be reduced or minimized by, for example, one or more of the following methods: bypassing the separator; draining the separator periodically; decreasing a surface area of exposed liquid in the separator; using an additional separator as a bypass separator while maintaining primary separator at a lower pressure; or adjusting a liquid level setpoint of the separator to maintain a short residence time.

In one embodiment, a fractional improvement (FracImp$_{hc}$) of hydrocarbon production for the process is at least 20%, at least 40%, at least 60%, at least 80%, or at least 100%. In some embodiments, the fractional improvement of hydrocarbon production is defined according to:

$$FracImp_{hc} = \left(\frac{Actual_{hc} - Base_{hc}}{Max_{hc} - Base_{hc}}\right),$$

where: Actual$_{hc}$ is an actual hydrocarbon production yield of the process; Base$_{hc}$ is a base case hydrocarbon yield when an average composition of the regeneration gas stream over the heating step is allowed to condense in the separator without reducing the amount of liquid hydrocarbons exposed by the separator to the regeneration stream; and Max$_{hc}$ is a theoretical best-case hydrocarbon yield for which liquids are instantaneously removed from the separator.

Figure 4:
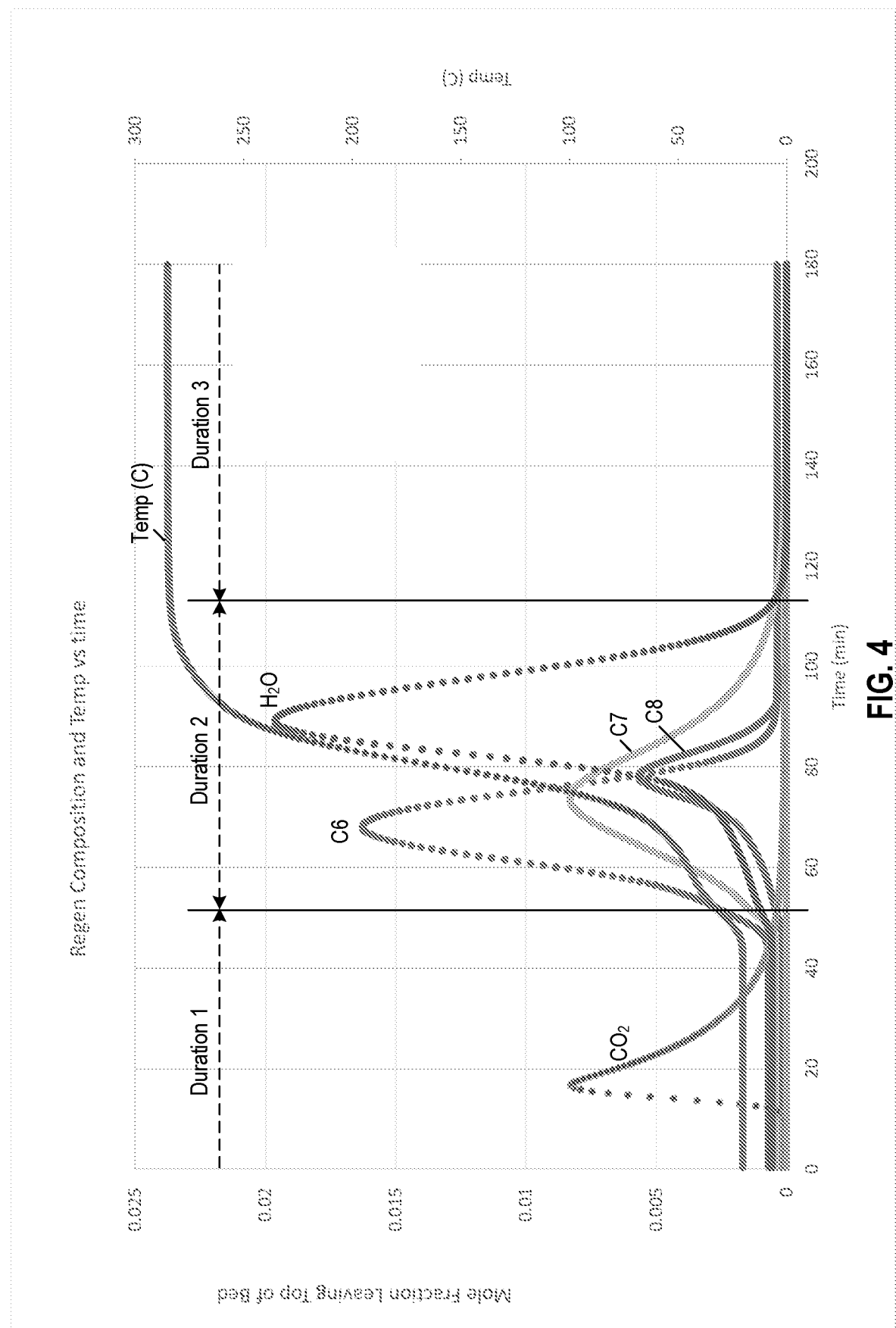
FIG. 4 shows a plot of simulated desorption gas composition versus time for various gaseous components leaving a bed in regeneration.

FIG. 4 shows a plot of simulated desorption gas composition versus time for various gaseous components leaving a bed in regeneration (e.g., mole fractions leaving the vessel of the adsorbent bed 121). During times of peak concentration, the components will generally be most easily condensed. In some embodiments, the separator may be bypassed or evacuated at times at which there is a lack of condensable components, for example, at the point at which the mole fraction of one or more of the components reaches or approaches zero, to reduce, eliminate, or minimize the vaporization of liquids present in the separator.

The plot of FIG. 4 illustrates three different durations of interest to various embodiments described herein. Durations 1 and 3 correspond to durations in the regeneration cycle for which an average C5+ hydrocarbon content of the regeneration stream is reduced or minimal. In some embodiments, Duration 1 ends before a first C5 or C6 hydrocarbon mole fraction in the gaseous phase reaches a peak (e.g., before 50%, before 40%, before 30%, before 20%, or before 10% of the peak mole fraction of, for example, the C6 mole fraction). In some embodiments, Duration 3 begins after a peak mole fraction of a C7, C8, or C9 hydrocarbon peak in the gaseous phase is reached (e.g., after 50%, after 40%, after 30%, after 20%, or after 10% of the peak mole fraction of the C7, C8, or C9 hydrocarbon peak in the gaseous phase is reached). Duration 2 is defined to account for the duration between Durations 1 and 3, and corresponds to a duration at which C5+ hydrocarbons are present in the gaseous phase leaving the adsorbent bed being regenerated.

Figure 5:
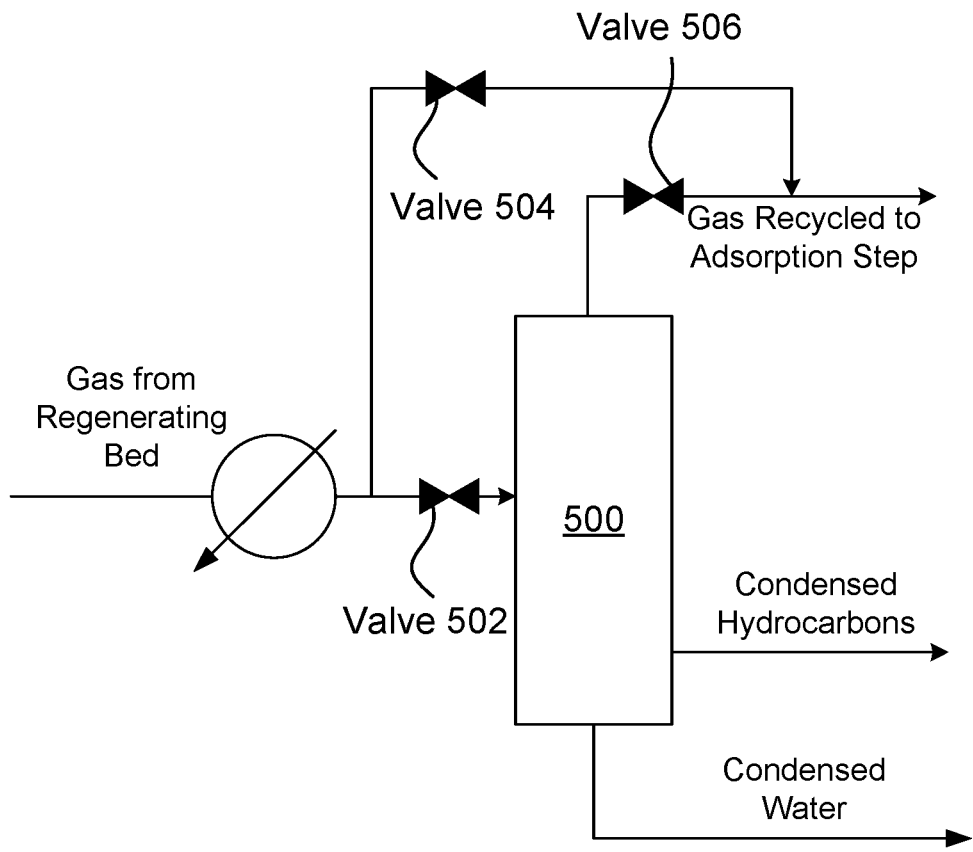
FIG. 5 is a schematic illustrating bypass of a separator in accordance with an embodiment.

FIG. 5 is a schematic illustrating bypass of a separator 500 (three-phase) in accordance with an embodiment. The separator 500 is configured to receive a regeneration stream from an adsorbent bed (e.g., the adsorbent bed 121), and is configured to separate the regeneration stream into a gas stream, a condensed hydrocarbon stream, and a water stream. A plurality of values 502, 504, 506 may be configured (e.g., controllable by a separate control device) to bypass the separator 500 and reduce an amount of liquid hydrocarbons exposed by the separator to the regeneration stream over one or more durations for which an average C5+ hydrocarbon content of the regeneration stream is reduced or minimal (e.g., Durations 1 and 3 of FIG. 4). For these durations, bypass of the separator 500 occurs when the valves 502 and 506 are closed and the valve 504 is open, which prevents re-vaporization of liquefied C5+ hydrocarbons into the regeneration stream. In some embodiments, liquid hydrocarbons in the separator 500 are completely drained or are drained to a low level during bypass. Outside of these durations (e.g., Duration 2), the valves 502 and 506 are open and the valve 504 is closed.

In some embodiments, the bypass configuration may result in improved performance over the configuration of FIG. 3. In some embodiments, a control unit may be utilized adjust the valves before the separator based on the mole fractions of the components in the regeneration bas stream, which will allow for the separator to be bypassed when no liquids are being condensed. In some embodiments, the control unit may be used to periodically drain the separator to remove liquids for which vaporization can occur. In some embodiments, a surface area of the exposed liquid in the separator may be reduced during periods of low or zero condensation.

Figure 6:
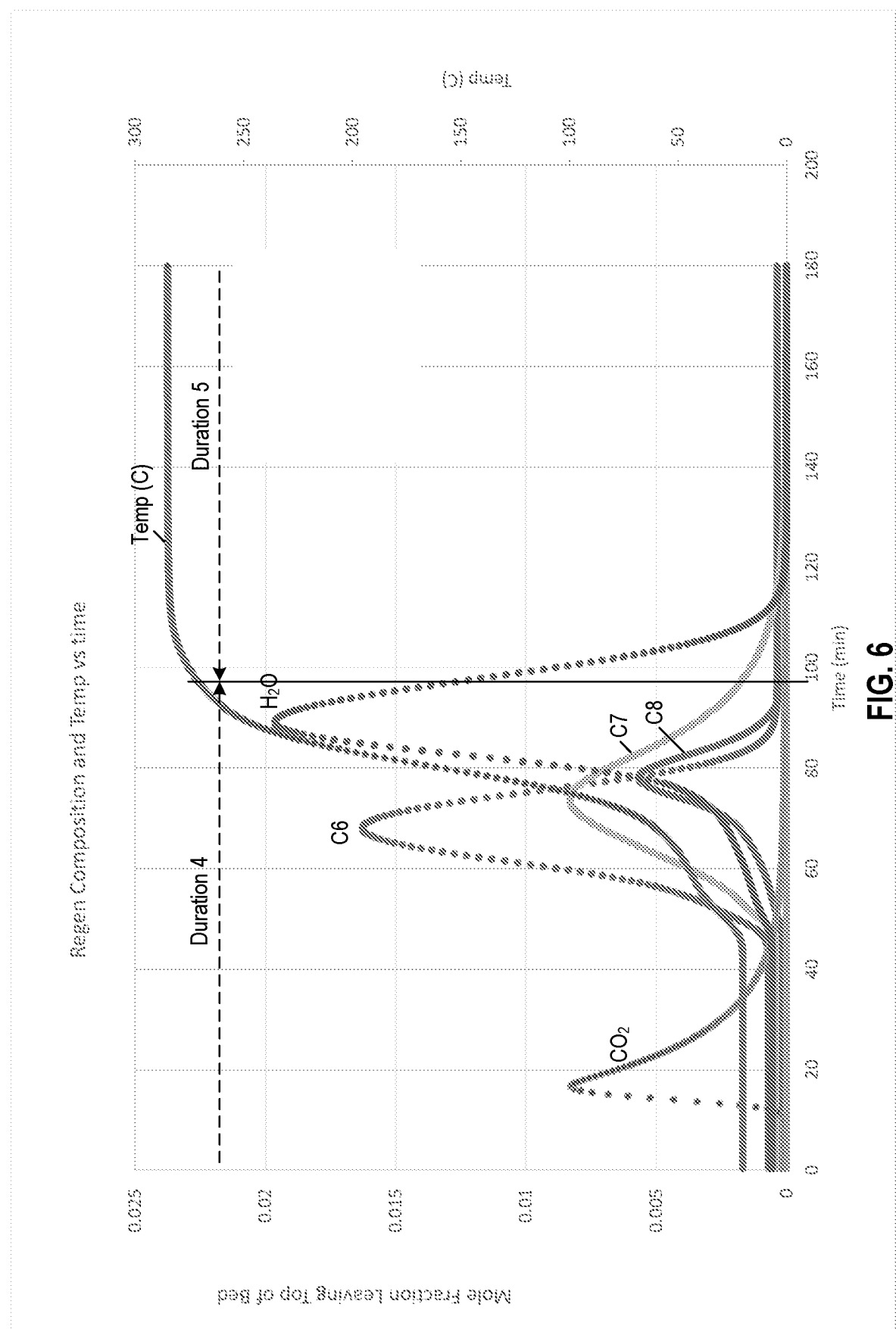
FIG. 6 illustrates two different durations of interest to various embodiments described herein.

The plot of FIG. 6 illustrates two different durations of interest to various embodiments described herein. Duration 5 begins after a peak mole fraction of a C7, C8, or C9 hydrocarbon peak in the gaseous phase is reached (e.g., after 50%, after 40%, after 30%, after 20%, or after 10% of the peak mole fraction of the C7, C8, or C9 hydrocarbon peak in the gaseous phase is reached). Duration 4 is defined to occur before Duration 5.

Figure 7:
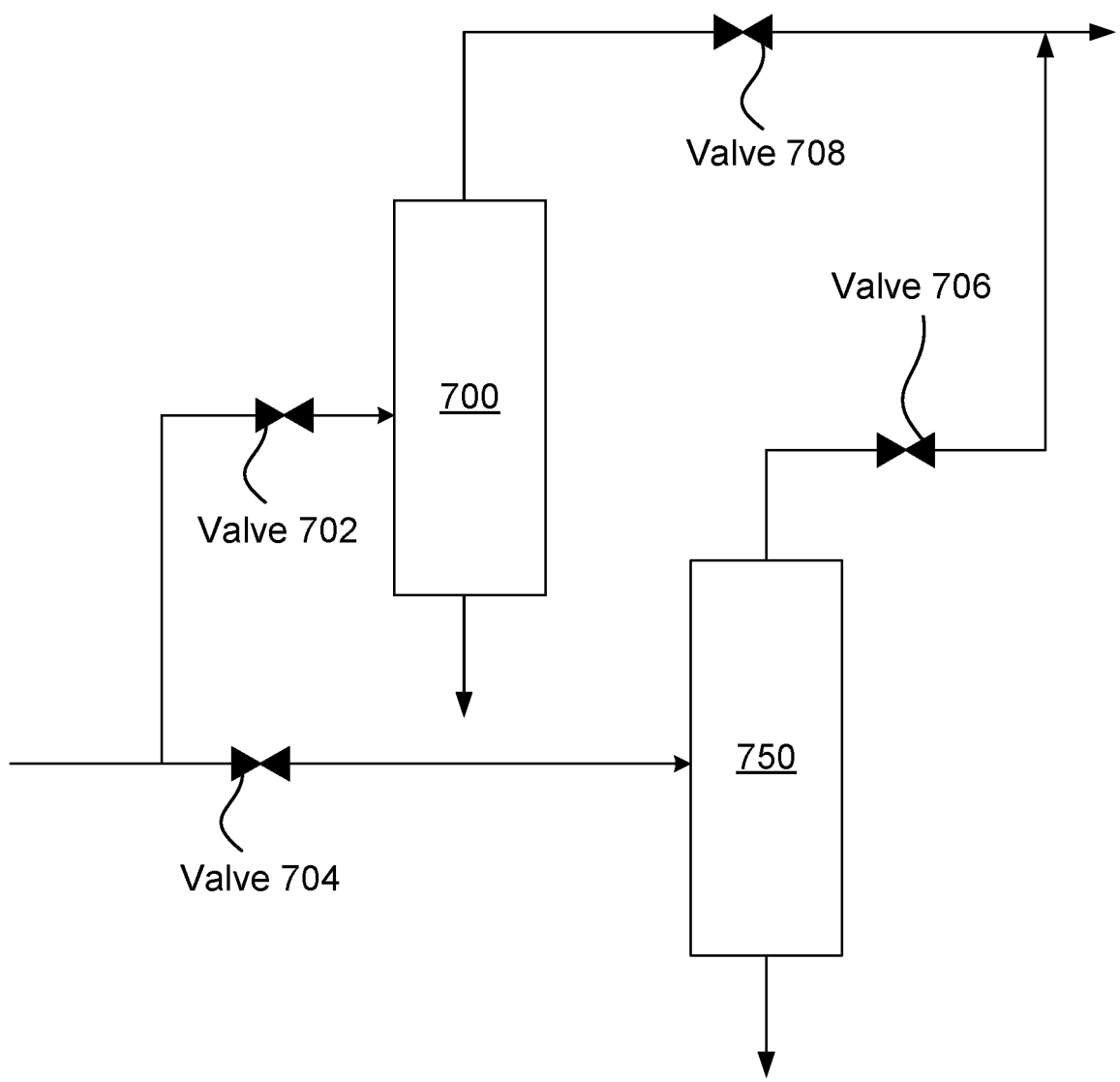
FIG. 7 is a schematic illustrating separators in a parallel configuration accordance with an embodiment.

FIG. 7 is a schematic illustrating separators 700 and 750 in a parallel configuration accordance with an embodiment. Both the separator 700 and 750 are configured to receive a regeneration stream from the adsorbent bed, and are configured to separate the regeneration stream into gas streams and condensed hydrocarbon streams. When the regeneration stream is fed to the separator 700, the valves 702 and 708 are open while the valves 704 and 706 are closed. The valves are configured to bypass the separator 700 (by closing valves 702 and 708 and opening valves 704 and 706) and diverting the regeneration stream to the separator 750 over a duration for which an average C5+ hydrocarbon content of the regeneration stream is reduced or minimal (e.g., during Duration 5), which reduces the exposure of liquefied C6 and/or C7 hydrocarbons to the regeneration stream. In some embodiments, liquid hydrocarbons in the separator 700 are drained or reduced to a lower level during bypass. In some embodiments, if a significant mole fraction of C8 or C9 hydrocarbons are present during Duration 5 in the separator 750, the next regeneration cycle may instead start with feeding the regeneration stream to the separator 750 instead of the separator 700.

Figure 8:
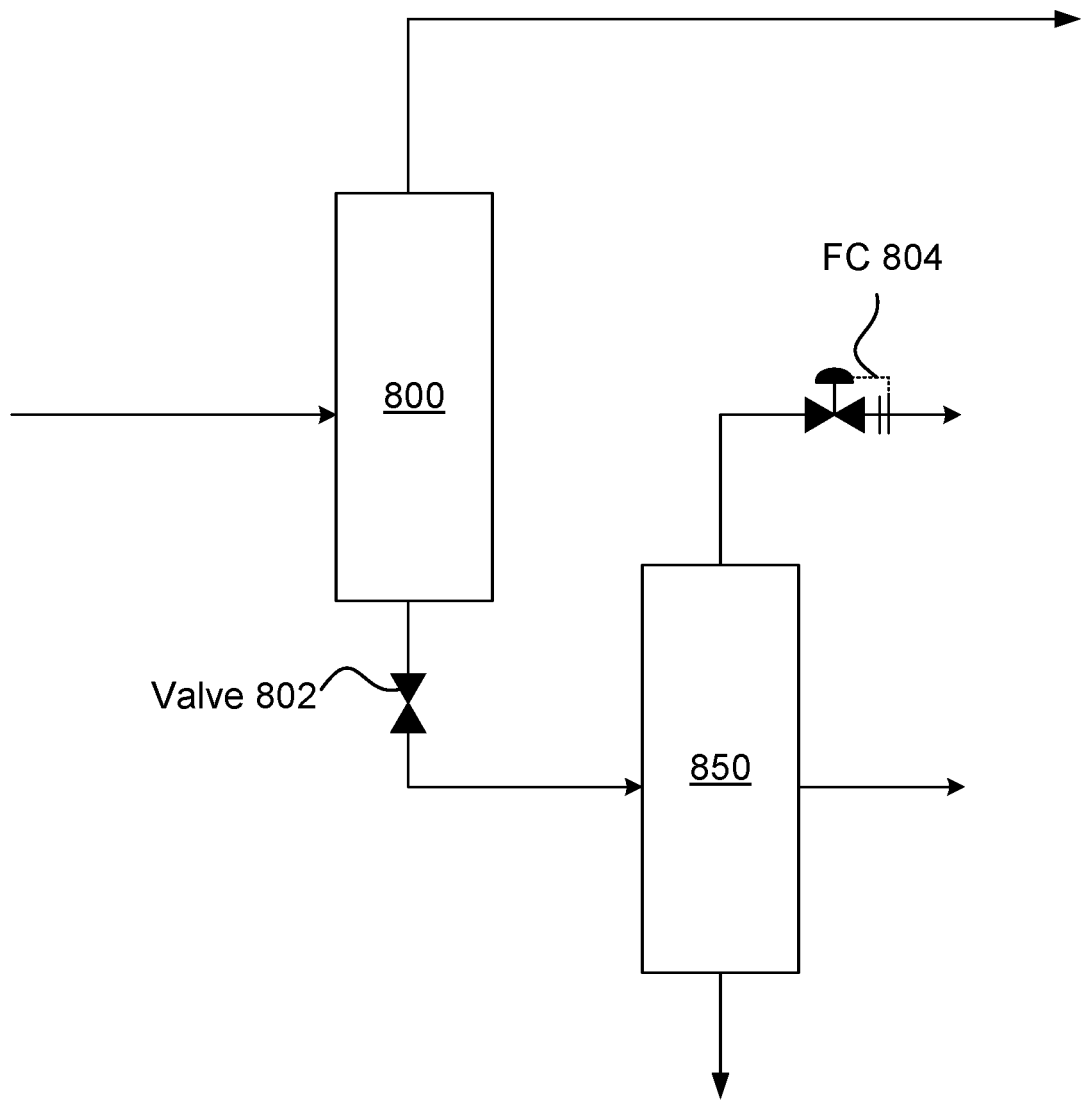
FIG. 8 is a schematic illustrating separators in a series configuration accordance with an embodiment.

FIG. 8 is a schematic illustrating separators 800 and 850 in a series configuration accordance with an embodiment. The separator 800 is configured to receive a regeneration stream from the adsorbent bed, and is configured to separate the regeneration stream into gas streams and condensed hydrocarbon streams. The separator 850 (three-phase) is configured to receive the condensed hydrocarbon stream from the separator 800 (when valve 802 is open) so as to maintain a minimal amount of condensed hydrocarbons in the separator 800 at any time during the regeneration cycle (independently of Durations 1-5). A flow controller (FC) 804 may be used at the gaseous phase outlet of the separator 850 to maintain constant flow.

Figure 9:
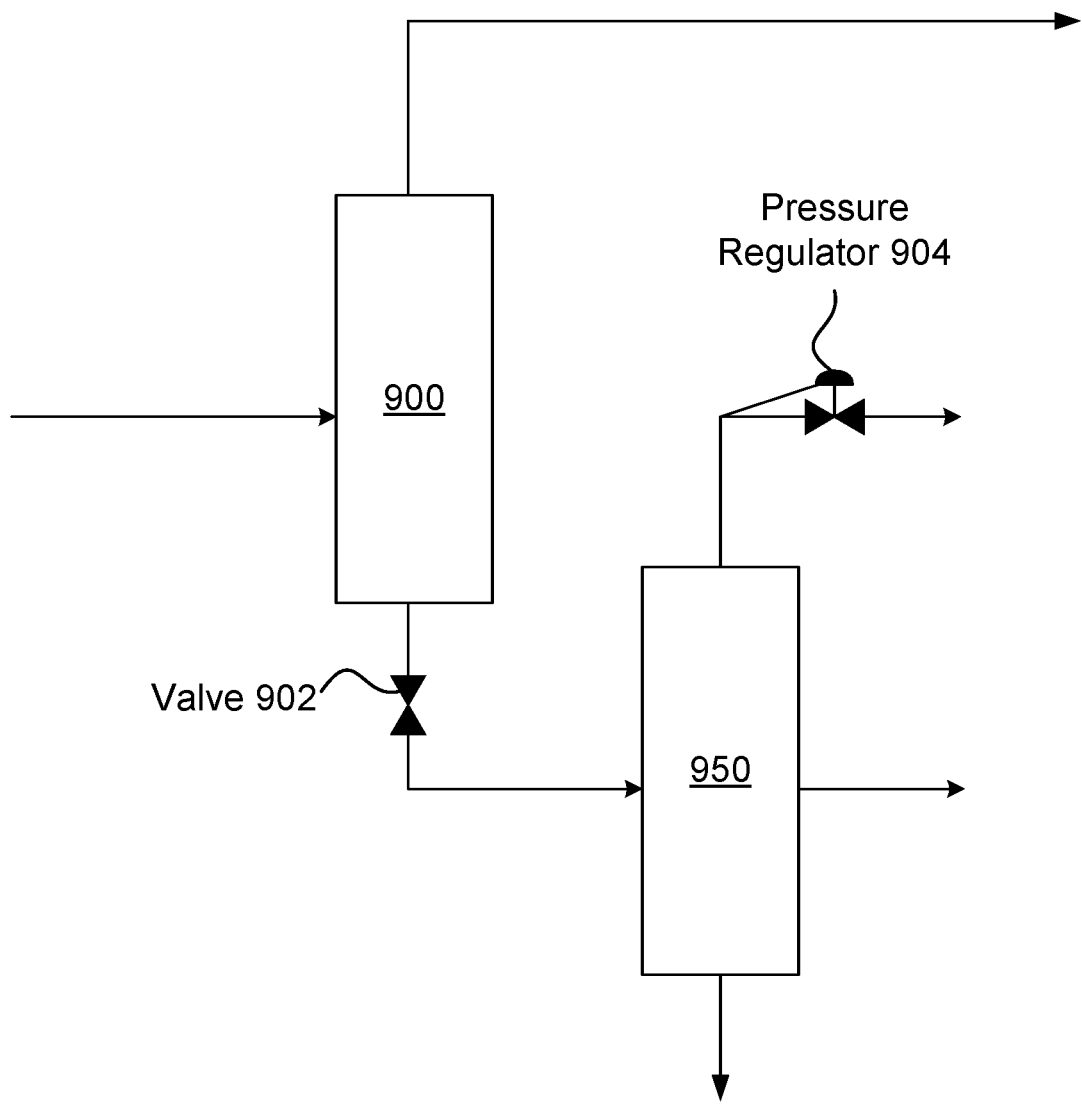
FIG. 9 is a schematic illustrating separators in a series configuration accordance with a further embodiment.

FIG. 9 is a schematic illustrating separators 900 (two-phase) and 950 (three-phase) in a series configuration accordance with an embodiment. The schematic of FIG. 9 is similar to that of FIG. 8, with the separator 950 being configured to receive the condensed hydrocarbon stream from the separator 900 (when valve 902 is open). In some embodiments, the separator 900 is configured to maintain a residence time of condensed hydrocarbons from 0.5 to minutes (e.g., 0.5 to 10 minutes). As used herein, "residence time" refers to a volume of a vessel of a separator used for liquid hydrocarbon storage (e.g., in cubic meters) divided by a liquid hydrocarbon volumetric flow rate at all inlets of the separator (e.g., in cubic meters per minute). In some embodiments, the separator 900 may utilize a controller that is configured to adjust a level setpoint of liquid hydrocarbons in the separator 900. In some embodiments, the separator 900 is configured to target, for example, a 0.5-10 minute (e.g., 3 minute) residence time at a maximum flow rate. In some embodiments, the separator 950 is maintained at a lower pressure than the separator 900 so as to allow for a 5-60 minute (e.g., 10 minute) residence time at a maximum flow rate. In some embodiments, a pressure regulator 904 is used to maintain a constant pressure of the gaseous phase leaving the separator 950.

In some embodiments, a single separator configuration may be utilized, where the separator is configured to maintain a minimum residence time of condensed hydrocarbons from minutes to 10 minutes for all liquid hydrocarbon inlet flows (i.e., while there is a non-zero flow rate into the separator). In some embodiments, the separator is configured to reduce a level setpoint of liquid hydrocarbons in response to a peak inlet hydrocarbon flow being observed or detected. In some embodiments, the separator is configured to reduce the hydrocarbon level setpoint by 5% to 95% in response to a peak inlet hydrocarbon flow being observed or detected. In some embodiments, the separator is configured to reduce the hydrocarbon level setpoint by 5% to 10%, by 10% to 15%, 15% to 20%, by 20% to 25%, 25% to 30%, by 30% to 35%, 35% to 40%, by 40% to 45%, 45% to 50%, by 50% to 55%, 55% to 60%, by 60% to 65%, 65% to 70%, by 70% to 75%, 75% to 80%, by 80% to 85%, by 85% to 90%, by 90% to 95%, or within any subrange defined therebetween (e.g., from 25% to 75%).

In some embodiments, the separator is configured to reduce a volume of stored liquid hydrocarbons by 5% to 95% in response to a peak inlet hydrocarbon flow being observed or detected. In some embodiments, the separator is configured to reduce a volume of stored liquid hydrocarbons by 5% to 10%, by 10% to 15%, 15% to 20%, by 20% to 25%, 25% to 30%, by 30% to 35%, 35% to 40%, by 40% to 45%, 45% to 50%, by 50% to 55%, 55% to 60%, by 60% to 65%, 65% to 70%, by 70% to 75%, 75% to 80%, by 80% to 85%, by 85% to 90%, by 90% to 95%, or within any subrange defined therebetween.

In some embodiments, the minimum residence time (e.g., corresponding to a maximum inlet flow rate during a regeneration cycle) is from 0.5 minutes to 1 minute, 1 minute to 1.5 minutes, 1.5 minutes to 2 minutes, 2 minutes to 2.5 minutes, 2.5 minutes to 3 minutes, 3 minutes to 3.5 minutes, 3.5 minutes to 4 minutes, 4 minutes to 4.5 minutes, 4.5 minutes to 5 minutes, 5 minutes to 5.5 minutes, 5.5 minutes to 6 minutes, 6 minutes to 6.5 minutes, 6.5 minutes to 7 minutes, 7 minutes to 7.5 minutes, 7.5 minutes to 8 minutes, 8 minutes to 8.5 minutes, 8.5 minutes to 9 minutes, 9 minutes to 9.5 minutes, 9.5 minutes to 10 minutes, or within any subrange defined therebetween. In some embodiments, the minimum residence time is from 5 minutes to 10 minutes, 10 minutes to 15 minutes, 15 minutes to 20 minutes, 20 minutes to 25 minutes, 25 minutes to 30 minutes, 30 minutes to 35 minutes, 35 minutes to 40 minutes, 40 minutes to 45 minutes, 45 minutes to 50 minutes, 50 minutes to 55 minutes, 55 minutes to 60 minutes, or within any subrange defined therebetween.

Figure 10:
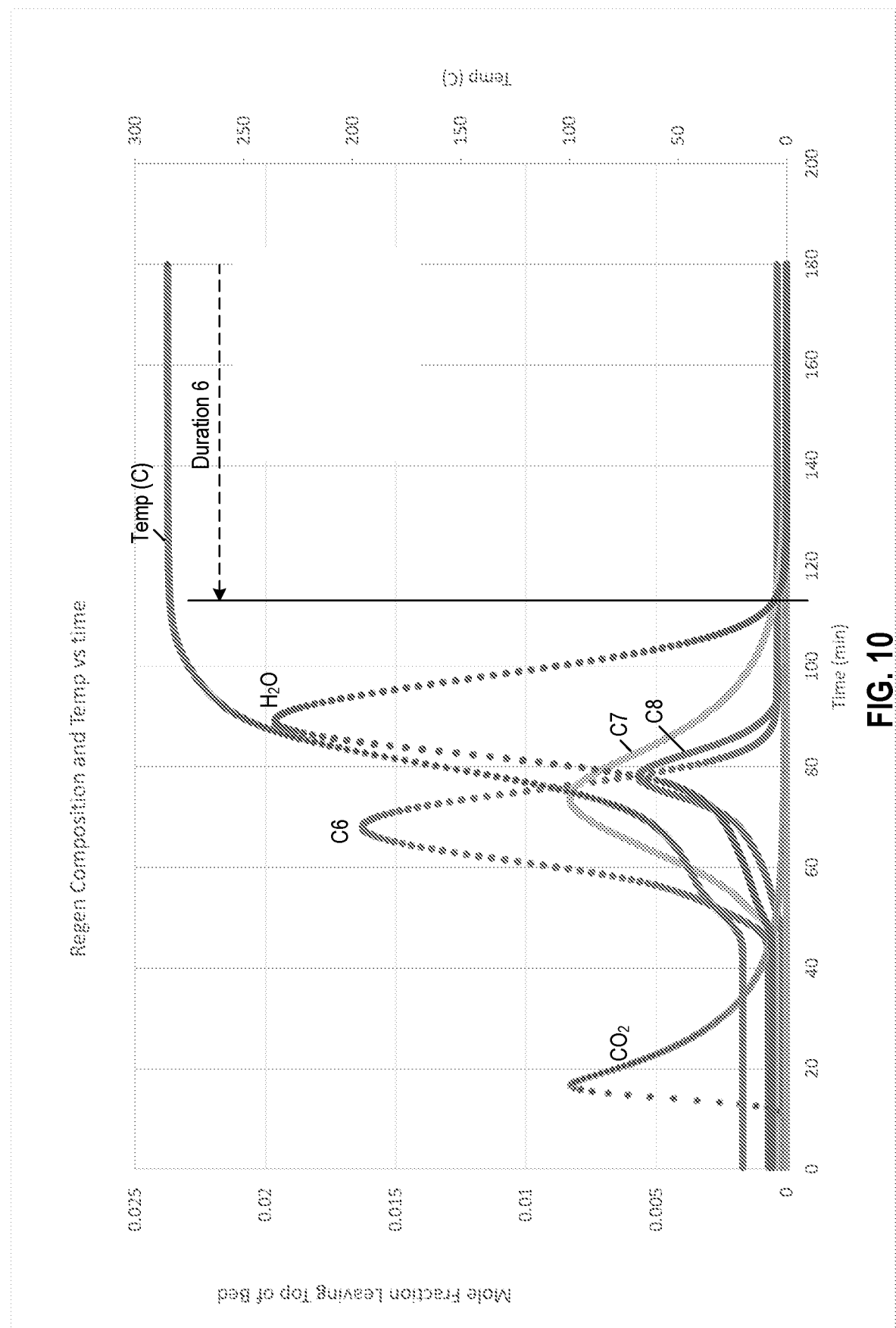
FIG. 10 is a plot illustrates a duration of interest to various embodiments described herein.

FIG. 10 is a plot illustrates a duration of interest to various embodiments described herein. Duration 6 begins after a peak mole fraction of a C7, C8, or C9 hydrocarbon peak in the gaseous phase is reached (e.g., after 50%, after 40%, after 30%, after 20%, or after 10% of the peak mole fraction of the C7, C8, or C9 hydrocarbon peak in the gaseous phase is reached).

Figure 11:
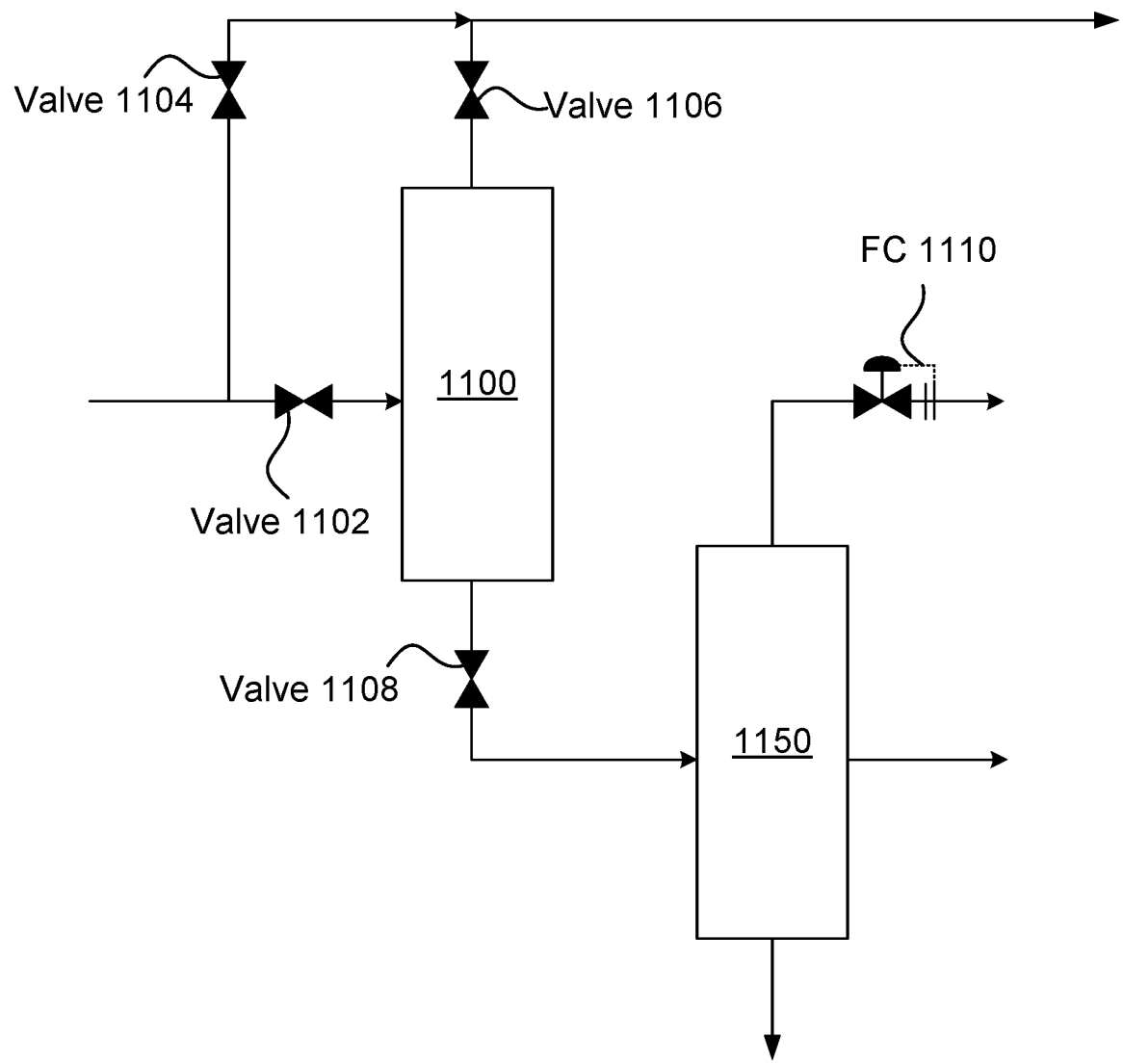
FIG. 11 is a schematic illustrating separators in a series configuration accordance with a further embodiment.

FIG. 11 is a schematic illustrating separators 1100 (two-phase) and 1150 (three-phase) in a series configuration accordance with an embodiment. The schematic of FIG. 11 is similar to that of FIG. 8 and includes a flow controller 1110, but further includes additional valves 1102, 1104, 1106, 1108 to enable bypass of the separator 1100 over durations for which an average C5+ hydrocarbon content of the regeneration stream is reduced or minimal (e.g., Duration 6). In some embodiments, during bypass of the separator 1100, flow into the separator 1150 is allowed to drop off, and the inlets to the separator 1150 can be closed off.

Figure 12:
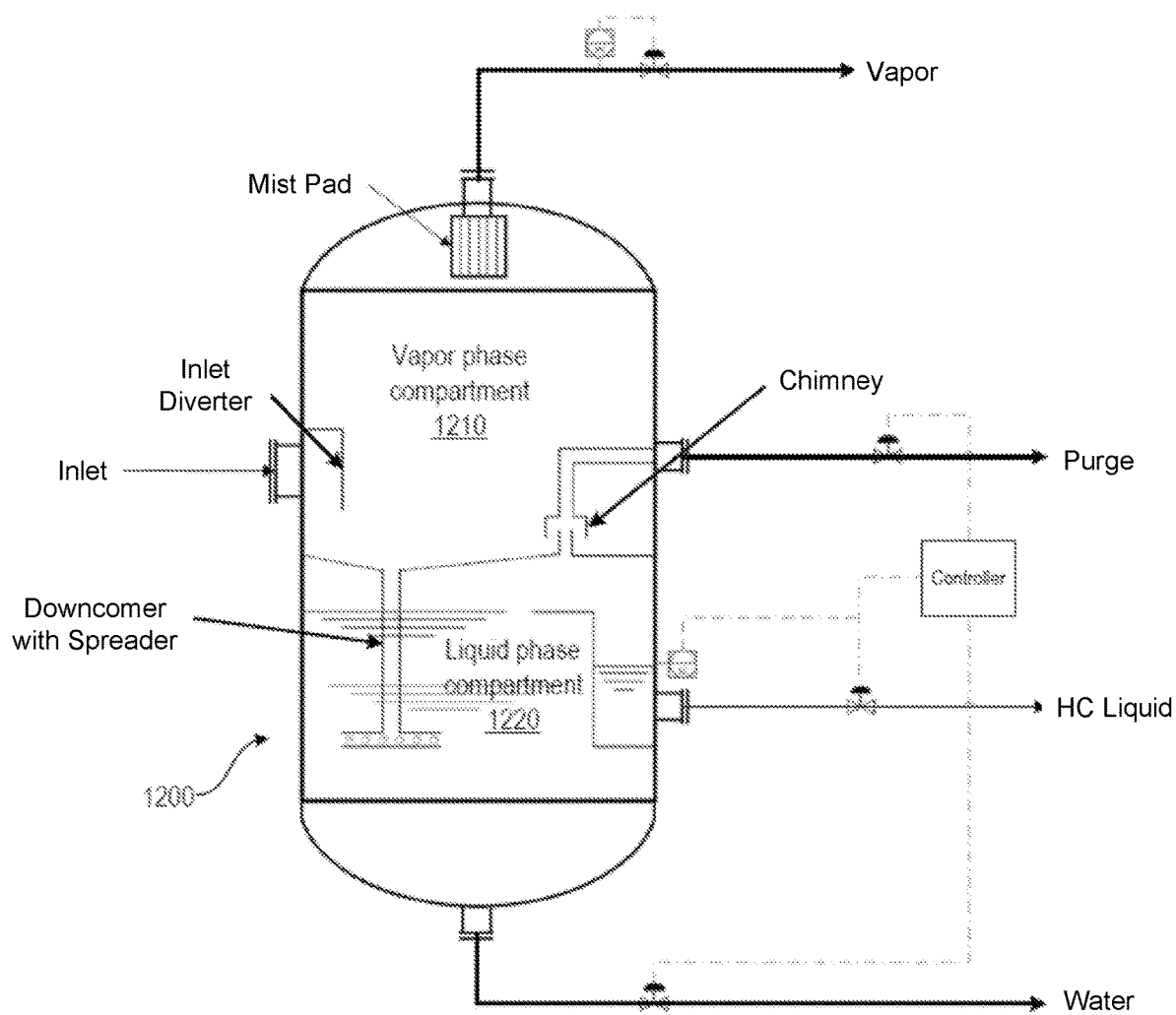
FIG. 12 is a schematic of a separator configured to control an amount of liquid hydrocarbons exposed to a gaseous phase in accordance with an embodiment.

FIG. 12 is a schematic of a separator 1200 configured to control an amount of liquid hydrocarbons exposed to a gaseous phase in accordance with an embodiment. The separator 1200 is configured to receive, from a an adsorbent bed in regeneration, a regeneration stream an inlet. The regeneration stream is diverted into a vapor phase compartment 1210 via an inlet diverter. An outlet above the vapor phase compartment 1210 allows for the vapor phase of the regeneration stream to exit the separator 1200 and return to the adsorbent bed, be diverted to a different adsorbent bed, or stored elsewhere. A downcomer and spreader are adapted to separate liquid hydrocarbons from the vapor phase and divert the liquid hydrocarbons to a liquid phase compartment 1220. A chimney is disposed above the liquid phase compartment 1220 to advantageously divert a majority of vapor from the liquid phase compartment to a separate outlet for purging vaporized heavy hydrocarbons (e.g., C5+ hydrocarbons). An outlet from the liquid phase compartment 1220 can be used to drain liquid hydrocarbons from the liquid phase compartment 1220. In some embodiments, a level sensor may be configured to maintain and adjust a level of the liquid hydrocarbons in the liquid phase compartment 1220. At the bottom of the separator 1200 is an outlet to drain liquid water that has accumulated in the liquid phase compartment 1220. A controller may be used to regulate valves that control the flow from the various outlets, as well as adjust the level setpoint of the liquid hydrocarbons. In some embodiments, the controller adjusts the level setpoint over time. For example, if the level of liquid hydrocarbons in the liquid phase compartment 1220 rises, then the liquid phase compartment 1220 is purged at a flow rate at least equal to a rate of volume of gas being displaced. In some embodiments, a minimum purge gas flow is maintained to avoid hydrocarbon vapors from the liquid phase compartment 1220 to mix with the vapor phase of the vapor phase compartment 1210.

Figure 13:
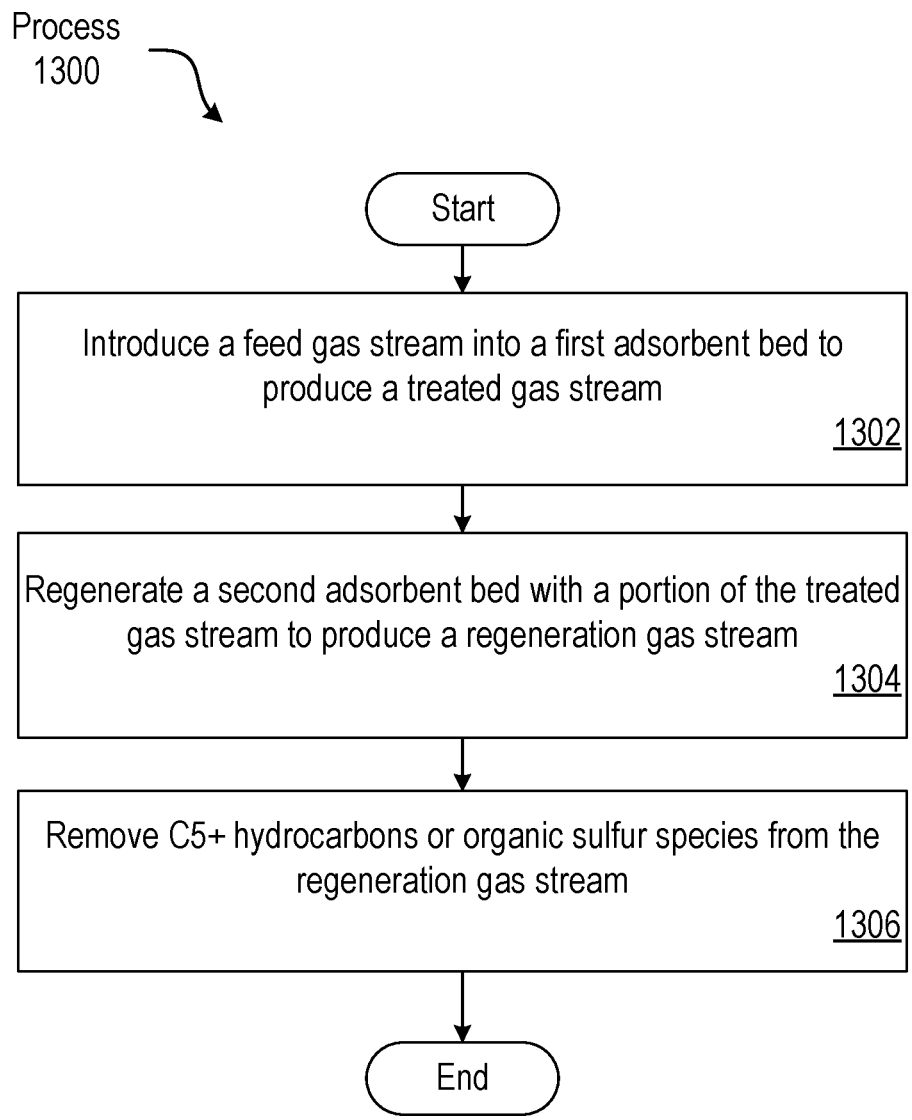
FIG. 13 illustrates a process of regeneration in an HRU system in accordance with at least one embodiment.

FIG. 13 illustrates a process 1300 of regeneration in an HRU system in accordance with at least one embodiment. At block 1302, a gas feed stream is introduced into a first adsorbent bed to produce a treated gas stream. In some embodiments, the adsorbent bed comprises one or more adsorbent layers, such as one or more of adsorbent layers 210, 220, or 230. In some embodiments, the first adsorbent bed comprises an amorphous silica adsorbent and/or an amorphous silica-alumina adsorbent, high-silica zeolite, zeolite X, zeolite 5A, or a combination thereof. In some embodiments, the first adsorbent bed comprises a zeolite comprising zeolite 3A, zeolite 4A, zeolite 5A, or zeolite 13X, or a combination thereof. In some embodiments, the zeolite is exchanged with an element selected from Li, Na, K, Mg, Ca, Sr, or Ba.

In some embodiments, the feed gas stream comprises C5+ hydrocarbons or organic sulfur species (e.g., mercaptans). In some embodiments, the feed gas stream (e.g., stream 101) comprises a natural gas feed stream. In some embodiments, the feed gas stream comprises predominately methane (i.e., at least 50% methane on a molar basis). In some embodiments, the feed gas stream comprises predominately $CO_2$ (i.e., at least 50% $CO_2$ on a molar basis). In some embodiments, the feed gas stream 101 is mixed with a regeneration gas stream prior to being introduced into the first adsorbent bed.

In some embodiments, the feed stream is introduced into the first adsorbent bed (e.g., adsorbent bed 120) as part of a TSA process. The TSA process may have an adsorption cycle time of less or equal to about 8 hours, about 7 hours, about 6 hours, about 5 hours, about 4 hours, about 3 hours, about 2 hours, or about 1 hour.

At block 1304, a second adsorbent bed (e.g., the adsorbent bed 121) is regenerated with a portion of the treated gas stream to produce a regeneration gas stream. In some embodiments, the adsorbent bed comprises one or more adsorbent layers, such as one or more of adsorbent layers 210, 220, or 230. In some embodiments, the second adsorbent bed comprises an amorphous silica adsorbent and/or an amorphous silica-alumina adsorbent, high-silica zeolite, zeolite X, zeolite 5A, or a combination thereof. In some embodiments, the second adsorbent bed comprises a zeolite comprising zeolite 3A, zeolite 4A, zeolite 5A, or zeolite 13X, or a combination thereof. In some embodiments, the zeolite is exchanged with an element selected from Li, Na, K, Mg, Ca, Sr, or Ba.

At block 1306, C5+ hydrocarbons or organic sulfur species are removed from the regeneration gas stream. In some embodiments, the C5+ hydrocarbons (including aromatic or aliphatic hydrocarbons) or organic sulfur species (e.g., mercaptans) are removed utilizing any of the separator embodiments described herein to separate condensed hydrocarbons and liquid water from the regeneration gas stream.

ILLUSTRATIVE EXAMPLES

The following examples based on simulations are set forth to assist in understanding the disclosure and should not, of course, be construed as specifically limiting the embodiments described and claimed herein. Such variations of the disclosed embodiments, including the substitution of all equivalents now known or later developed, which would be within the purview of those skilled in the art, and changes in formulation or minor changes in experimental design, are to be considered to fall within the scope of the embodiments incorporated herein.

Example 1

A simulation of the system 100 is performed by modifying the separator 124 such that no liquid is present therein when there are no gaseous species in the regeneration gas stream 104 to condense. The objective is to reduce the level of mercaptans in the feed gas 112. The feed gas is fed to the adsorbent bed 120 which contains 24,000 kg of adsorbent. The adsorption step is run for 120 minutes, and after the adsorption step the adsorbent bed 121 is heated with a portion of the product gas yielding a stream with the average composition as described by stream regeneration gas in Table 1 leaving the adsorbent bed 421 over the cycle. This stream is subsequently flashed at the actual compositions over the desorption cycle and it is further assumed that the liquids are removed from the separator as they are created. As can be seen in Table 1, the modified separator 124 is able to remove the methyl mercaptan ("m-mercaptan") at a level greater than comparative example 1 as evident by a lower buildup of methyl mercaptan in the feed to the adsorbent bed 120 as illustrated by the compositions in stream 102 compared to stream 101.

TABLE 1

| | Example 1 with stream definitions of FIG. 1 | | | | | |
|---|---|---|---|---|---|---|
| Stream No. | 101 | 102 | 103 | 104 | 106 | 117 |
| | | Total Feed to Adsorbent | Treated gas from Adsorbent | Regen gas from Tower in | Recycle Gas from Regen | HC Liquid and Water |
| Stream Name | Feed Gas | Bed | Bed | Regen | Separator | Disposal |
| Properties | | | | | | |
| Flow (lbmol/hr) | 49412 | 54120 | 53975 | 4837 | 4708 | 129 |
| Temp. (° .F) | 118 | 118 | 118 | 86 | 86 | 86 |
| Pressure (psia) | 1117 | 1110 | 1117 | 1054 | 1054 | 1054 |
| Component (mole %) | | | | | | |
| $N_2$ | 0.0000 | 0.0000 | 0.0000 | 0.0000 | 0.0000 | 0.0000 |
| $CO_2$ | 0.0030 | 0.0168 | 0.0030 | 0.1532 | 0.1611 | 0.0157 |
| C1 | 96.7621 | 96.7298 | 96.9963 | 94.0181 | 96.3903 | 7.2566 |
| C2 | 2.7759 | 2.7734 | 2.7810 | 2.6956 | 2.7472 | 0.8086 |
| C3 | 0.1103 | 0.1101 | 0.1104 | 0.1070 | 0.1077 | 0.0802 |
| iC4 | 0.0201 | 0.0200 | 0.0200 | 0.0194 | 0.0192 | 0.0277 |
| nC4 | 0.0401 | 0.0399 | 0.0400 | 0.0388 | 0.0379 | 0.0718 |

TABLE 1-continued

Example 1 with stream definitions of FIG. 1

| Stream No. | 101 | 102 Total Feed to Adsorbent Bed | 103 Treated gas from Adsorbent Bed | 104 Regen gas from Tower in Regen | 106 Recycle Gas from Regen Separator | 117 HC Liquid and Water Disposal |
|---|---|---|---|---|---|---|
| Stream Name | Feed Gas | | | | | |
| iC5 | 0.0098 | 0.0101 | 0.0097 | 0.0144 | 0.0138 | 0.0397 |
| nC5 | 0.0000 | 0.0000 | 0.0000 | 0.0000 | 0.0000 | 0.0000 |
| nC6 | 0.0050 | 0.0053 | 0.0048 | 0.0106 | 0.0083 | 0.0947 |
| nC7 | 0.0333 | 0.0354 | 0.0271 | 0.1198 | 0.0569 | 2.4121 |
| Benzene | 0.0249 | 0.0376 | 0.0054 | 0.3652 | 0.1710 | 7.4644 |
| nC8 | 0.0104 | 0.0121 | 0.0018 | 0.1179 | 0.0304 | 3.3148 |
| Toluene | 0.0000 | 0.0000 | 0.0000 | 0.0001 | 0.0000 | 0.0032 |
| nC9 | 0.0040 | 0.0044 | 0.0001 | 0.0477 | 0.0086 | 1.4763 |
| nC10 | 0.0034 | 0.0038 | 0.0000 | 0.0420 | 0.0074 | 1.3023 |
| nC11 | 0.0000 | 0.0000 | 0.0000 | 0.0001 | 0.0000 | 0.0027 |
| m-mercaptan | 0.0007 | 0.0025 | 0.0004 | 0.0239 | 0.0218 | 0.1278 |
| $H_2S$ | 0.0000 | 0.0000 | 0.0000 | 0.0000 | 0.0000 | 0.0000 |
| e-mercaptan | 0.0003 | 0.0010 | 0.0000 | 0.0109 | 0.0088 | 0.1014 |
| Xylenes | 0.0000 | 0.0000 | 0.0000 | 0.0000 | 0.0000 | 0.0000 |
| np-mercaptan | 0.0068 | 0.0139 | 0.0000 | 0.1555 | 0.0881 | 2.6041 |
| $H_2O$ | 0.1900 | 0.1840 | 0.0000 | 2.0598 | 0.1215 | 72.7961 |
| MeOH | 0.0000 | 0.0000 | 0.0000 | 0.0000 | 0.0000 | 0.0000 |

Comparative Example 1

In describing this example, reference is made to system 100 of FIG. 1 with the objective being to reduce the level of mercaptans in the feed 112. The feed gas 112 as described by stream 101 in Table 3 is fed to the adsorbent bed 120 which contains 24,000 kg of adsorbent. The adsorption step is run for 120 minutes, and after the adsorption step the adsorbent bed 121 is heated with a portion of the product gas yielding a stream with the average composition as described by stream 404 in Table 2 leaving the adsorbent bed 121 over the cycle. This stream is subsequently flashed at the average composition over desorption. As can be seen in Table 2, the separator 124 does not remove a majority of the methyl mercaptan as evident by the buildup of methyl mercaptan in the feed to the adsorbent bed 120 as illustrated by the compositions in stream 102 compared to stream 101.

TABLE 2

Comparative Example 1 with stream definitions of FIG. 1

| Stream No. | 101 | 102 Total Feed to Adsorbent Bed | 103 Treated gas from Adsorbent Bed | 104 Regen gas from Tower in Regen | 106 Recycle Gas from Regen Separator | 117 HC Liquid and Water Disposal |
|---|---|---|---|---|---|---|
| Stream Name | Feed Gas | | | | | |
| Properties | | | | | | |
| Flow (lbmol/hr) | 49411 | 54196 | 54049 | 4908 | 4785 | 123 |
| Temp. (° F.) | 118 | 118 | 118 | 500 | 86 | 86 |
| Pressure (psia) | 1117 | 1117 | 1117 | 1117 | 1116 | 1116 |
| Component (mole %) | | | | | | |
| $N_2$ | 0.3612 | 0.3611 | 0.3621 | 0.3509 | 0.3597 | 0.0087 |
| $CO_2$ | 0.0000 | 0.0009 | 0.0000 | 0.0097 | 0.0096 | 0.0142 |
| C1 | 96.4036 | 96.3577 | 96.6281 | 93.6419 | 95.8840 | 6.2231 |
| C2 | 2.7759 | 2.7732 | 2.7810 | 2.6951 | 2.7461 | 0.7071 |
| C3 | 0.1103 | 0.1101 | 0.1104 | 0.1070 | 0.1078 | 0.0724 |
| iC4 | 0.0201 | 0.0200 | 0.0200 | 0.0194 | 0.0192 | 0.0261 |
| nC4 | 0.0401 | 0.0399 | 0.0400 | 0.0388 | 0.0380 | 0.0696 |
| iC5 | 0.0098 | 0.0101 | 0.0097 | 0.0138 | 0.0130 | 0.0456 |
| nC5 | 0.0000 | 0.0000 | 0.0000 | 0.0000 | 0.0000 | 0.0000 |
| nC6 | 0.0050 | 0.0053 | 0.0048 | 0.0098 | 0.0080 | 0.0830 |
| nC7 | 0.0333 | 0.0365 | 0.0291 | 0.1115 | 0.0701 | 1.7274 |
| Benzene | 0.0249 | 0.0545 | 0.0107 | 0.4945 | 0.3604 | 5.7239 |
| nC8 | 0.0104 | 0.0144 | 0.0028 | 0.1307 | 0.0559 | 3.0503 |
| nC9 | 0.0040 | 0.0048 | 0.0002 | 0.0509 | 0.0132 | 1.5237 |
| nC10 | 0.0034 | 0.0036 | 0.0000 | 0.0399 | 0.0058 | 1.3685 |
| nC11 | 0.0000 | 0.0000 | 0.0000 | 0.0001 | 0.0000 | 0.0028 |
| m-mercaptan | 0.0007 | 0.0031 | 0.0006 | 0.0280 | 0.0277 | 0.0385 |
| e-mercaptan | 0.0003 | 0.0020 | 0.0001 | 0.0215 | 0.0199 | 0.0840 |
| np-mercaptan | 0.0068 | 0.0227 | 0.0000 | 0.2511 | 0.1874 | 2.7340 |
| $H_2O$ | 0.1900 | 0.1798 | 0.0000 | 1.9851 | 0.0742 | 76.4939 |

Figure 14:
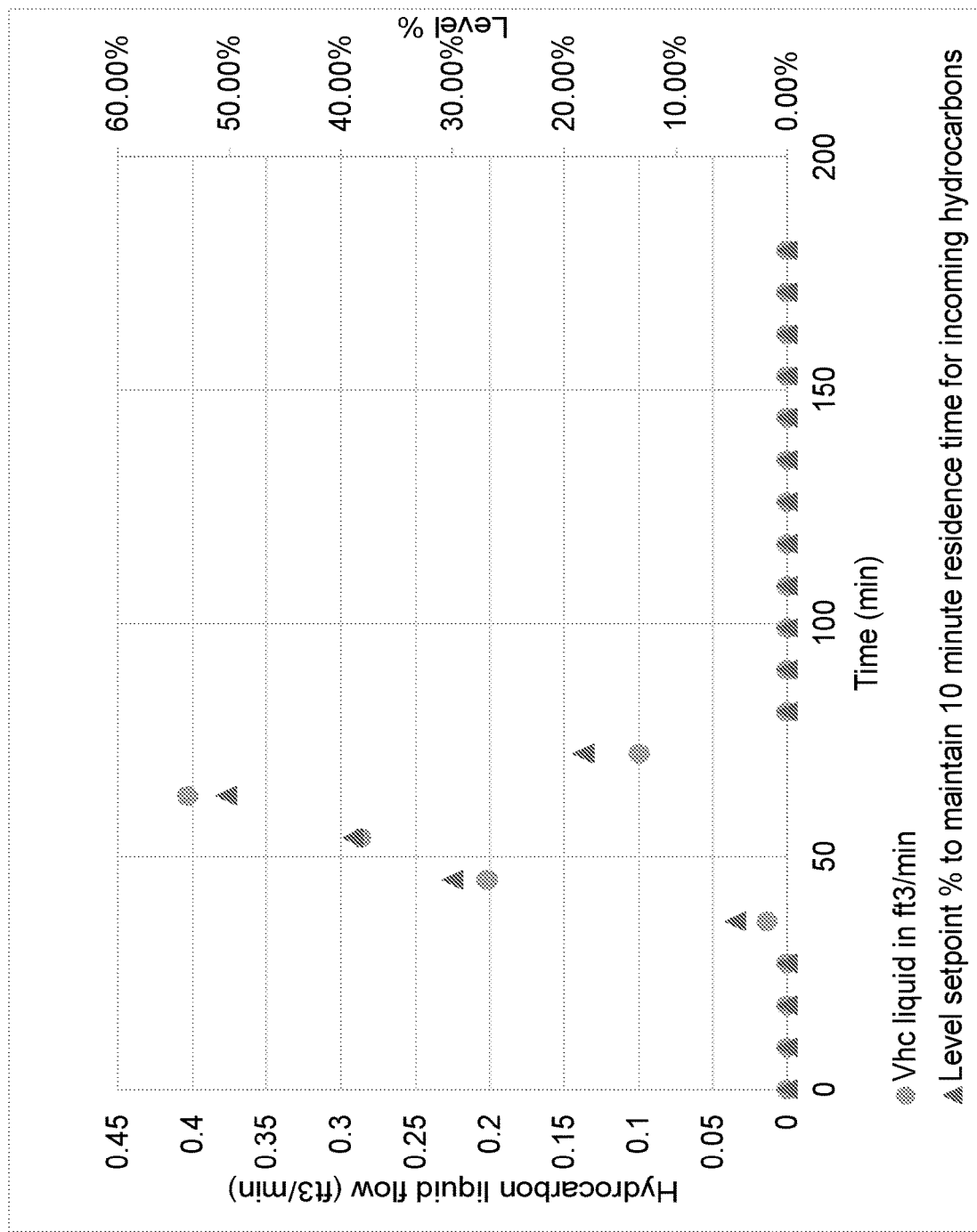
FIG. 14 is a plot showing level setpoints that maintain a constant residence time for incoming hydrocarbons into a separator.

Example 2: Level Setpoint to Maintain Constant Residence Time for Incoming Hydrocarbons In this example, the separator is a modeled as a horizontal cylindrical vessel. The separator receives a regeneration stream that has been passed to a cooler before entering the separator. A ten-minute residence time is achieved throughout the regeneration cycle for all inlet liquid hydrocarbon flows, with the volume for hydrocarbon storage changing throughout the regeneration cycle. This results in a peak volume at approximately 63 minutes, as illustrated by the plot of FIG. 14.

Comparative Example 2

Figure 15:
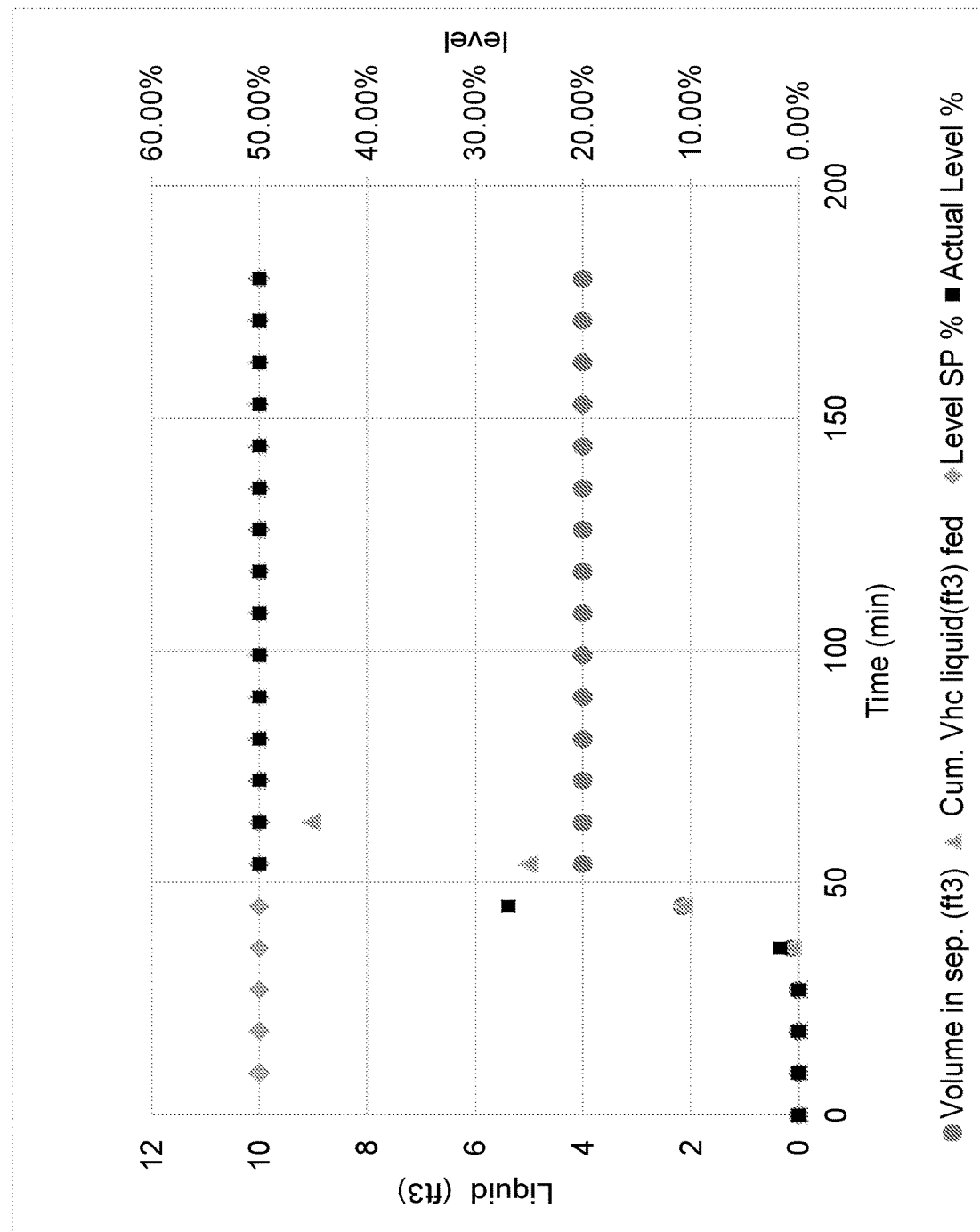
FIG. 15 is a plot showing the effect on liquid hydrocarbon volume in a separator when a level setpoint is constant throughout a regeneration cycle.

In this example, a regeneration stream is passed to a cooler then into a separator. The separator is again modeled as a horizontal cylindrical vessel. The height of hydrocarbon liquids set point in the separator is held constant throughout the regeneration cycle such that at a minimum residence time of 10 minutes is maintained for all liquid inlet flowrates into the separator. The net effect is the level setpoint is set to accommodate the highest liquid hydrocarbon inlet flows. This results in a storage of approximately 40% of the original hydrocarbons fed to the separator after peak liquid hydrocarbon flow at the separator inlet, as illustrated by the plot in FIG. 15. These stored liquid hydrocarbons have the potential to vaporize back into vapor stream leaving the separator after peak hydrocarbon production.

Example 3

Figure 16:
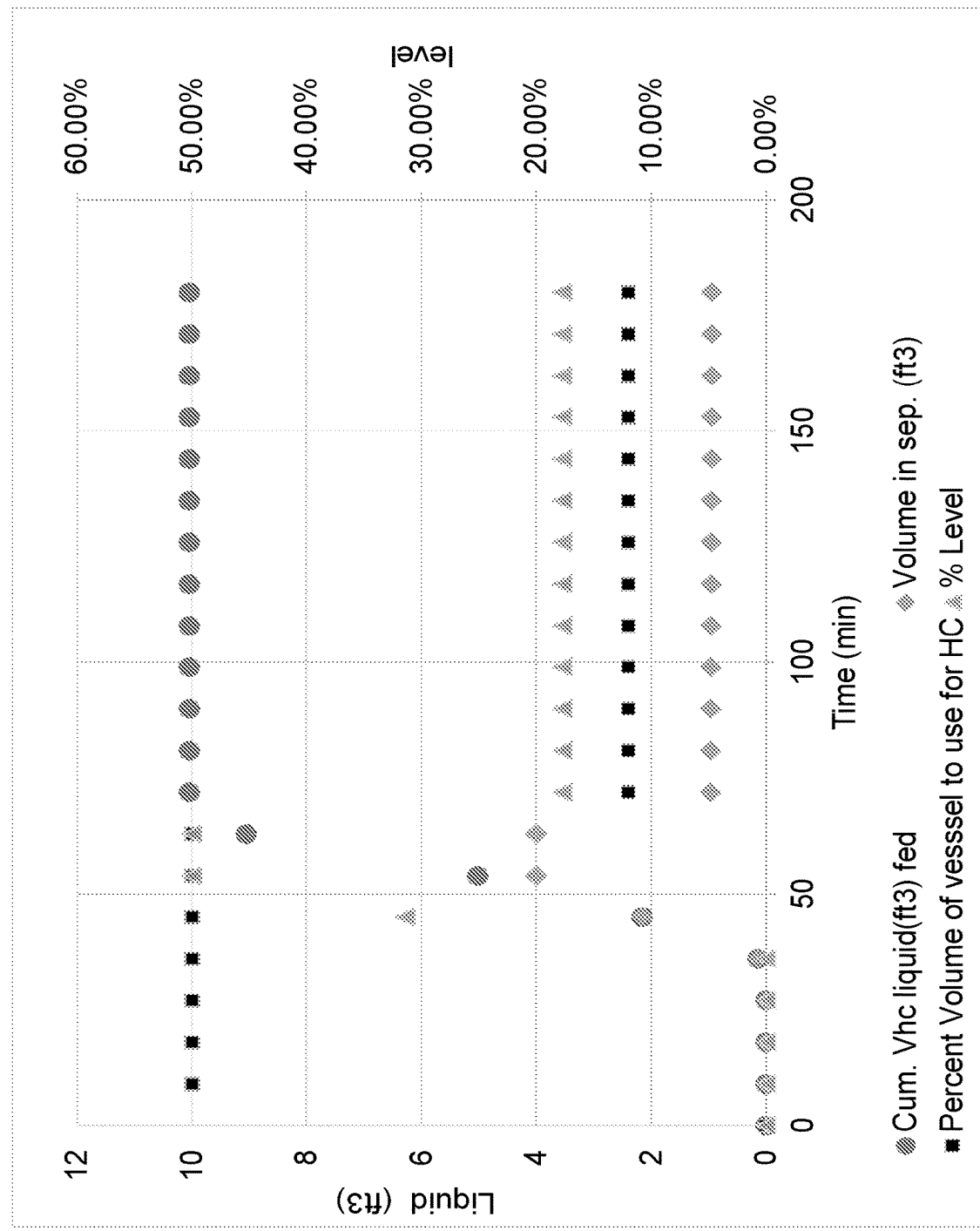
FIG. 16 is a plot showing the effect on liquid hydrocarbon volume in a separator when a level setpoint is reduced at a point during a regeneration cycle.

In this example, the liquid level setpoint is set to maintain a level that can retain the highest liquid inlet flow for 10 minutes. The separator is again modeled as a horizontal cylindrical vessel. After a period of the residence time away from the highest liquid inlet flow, the level setpoint is set to 25% of the original level setpoint. This results in lower liquids stored in the vessel (approximately 10% of all that is fed to the vessel), as illustrated by the plot in FIG. 16. Due to the lower volume of liquids stored in the separator, less hydrocarbons will vaporize back into the vapor stream leaving the separator. Furthermore, since the separator is modeled as a horizontal cylindrical vessel, the surface area for hydrocarbons that can evaporate will be reduced, thus minimizing the vaporization of previously condensed hydrocarbons.

In the foregoing description, numerous specific details are set forth, such as specific materials, dimensions, processes parameters, etc., to provide a thorough understanding of the embodiments of the present disclosure. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion.

As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form.

Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment, and such references mean "at least one".

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A process comprising:
   introducing a feed gas stream comprising C5+ hydrocarbons or organic sulfur species into a first adsorbent bed to produce a treated gas stream;
   regenerating a second adsorbent bed with a portion of the treated gas stream to produce a regeneration gas stream;
   introducing the regeneration stream into a separator to separate a gaseous phase of the regeneration gas stream from liquid hydrocarbon and/or liquid water phases;
   reducing an amount of liquid hydrocarbons exposed by the separator to the regeneration stream over one or more durations for which an average C5+ hydrocarbon content of the regeneration stream is reduced or minimal; and
   mixing the separated gaseous phase with the feed gas stream.

2. A process comprising:
   introducing a feed gas stream comprising C5+ hydrocarbons or organic sulfur species into a first adsorbent bed to produce a treated gas stream;
   regenerating a second adsorbent bed with a portion of the treated gas stream to produce a regeneration gas stream;
   introducing the regeneration stream into a separator to separate a gaseous phase of the regeneration gas stream from liquid hydrocarbon and/or liquid water phases;
   reducing an amount of liquid hydrocarbons exposed by the separator to the regeneration stream,
   wherein a fractional improvement (FracImp$_{hc}$) of hydrocarbon production for the process is at least 20%, at least 40%, at least 60%, at least 80%, or at least 100%, and wherein the fractional improvement of hydrocarbon production is defined according to:

$$FracImp_{hc} = \left(\frac{Actual_{hc} - Base_{hc}}{Max_{hc} - Base_{hc}}\right),$$

where:
   Actual$_{hc}$ is an actual hydrocarbon production yield of the process,
   Base$_{hc}$ is a base case hydrocarbon yield when an average composition of the regeneration gas stream over the heating step is allowed to condense in the separator without reducing the amount of liquid hydrocarbons exposed by the separator to the regeneration stream, and $Max_{hc}$ is a best-case hydrocarbon yield for which liquids are instantaneously removed from the separator; and mixing the separated gaseous phase with the feed gas stream.

3. The process of claim 1, wherein a first duration of the one or more durations ends before a peak mole fraction of a C5 or C6 hydrocarbon peak in the gaseous phase is reached.

4. The process of claim 3, wherein the first duration ends before 50% of the peak mole fraction of the C5 or C6 hydrocarbon peak in the gaseous phase is reached.

5. The process of claim 1, wherein a second duration of the one or more durations begins after a peak mole fraction of a C7, C8, or C9 hydrocarbon peak in the gaseous phase is reached.

6. The process of claim 5, wherein the second duration begins after 10% of the peak mole fraction of the C7, C8, or C9 hydrocarbon peak in the gaseous phase is reached.

7. The process of claim 1, wherein reducing the amount of liquid hydrocarbons exposed by the separator to the gaseous phase comprises:

reducing the surface area of liquid hydrocarbons in the separator during the one or more durations.

8. The process of claim 7, wherein reducing the surface area comprises lowering a liquid level control setpoint.

\* \* \* \* \*